(12) United States Patent
Raj et al.

(10) Patent No.: US 9,151,749 B2
(45) Date of Patent: Oct. 6, 2015

(54) ASSAY DEVICE COMPRISING BUBBLE-FORMING MEANS

(75) Inventors: Balbir Raj, Bedford (GB); David Tolley, Bedford (GB)

(73) Assignees: Alere Switzerland GMBH, Zug (CH); SPD Swiss Precision Diagnostics GMBH, Geneva (CH); David Trolley, Bedford (GB)

( * ) Notice: Subject to any disclaimer, the term of this patent is extended or adjusted under 35 U.S.C. 154(b) by 533 days.

(21) Appl. No.: 12/937,465

(22) PCT Filed: Apr. 9, 2009
(Under 37 CFR 1.47)

(86) PCT No.: PCT/GB2009/050354
§ 371 (c)(1),
(2), (4) Date: Jun. 1, 2011

(87) PCT Pub. No.: WO2009/125227
PCT Pub. Date: Oct. 5, 2009

(65) Prior Publication Data
US 2011/0300555 A1    Dec. 8, 2011

(30) Foreign Application Priority Data

Apr. 12, 2008  (GB) .................................. 0806771.2
Nov. 26, 2008  (GB) .................................. 0821552.7

(51) Int. Cl.
*C12Q 1/00*        (2006.01)
*G01N 33/543*    (2006.01)
(Continued)

(52) U.S. Cl.
CPC .... *G01N 33/54366* (2013.01); *B01L 3/502738* (2013.01); *B01L 3/502746* (2013.01); *G01N 33/581* (2013.01); *B01L 2200/0621* (2013.01);
(Continued)

(58) Field of Classification Search
CPC ................. B01L 2300/0816; B01L 2400/046; B01L 3/5027; C12Q 1/26; C12Q 1/30; C12Q 2304/44; G01N 2021/054
USPC ........ 422/305, 408, 412, 414, 417, 425, 68.1, 422/82.05, 119; 435/287.5, 287.2, 287.9, 4, 435/7.1, 7.9, 7.94, 300.1, 807, 25, 27; 73/1.16, 152.18, 152.29, 861.41; 436/518, 501, 510, 539, 540, 148
See application file for complete search history.

(56) References Cited

U.S. PATENT DOCUMENTS 4,263,405 A  *  4/1981  Melnick et al. ............ 435/287.5
4,311,666 A        1/1982  Hultman et al.
(Continued)

FOREIGN PATENT DOCUMENTS

JP          63222257 A      9/1988
WO     WO-2008025945 A1   3/2008

*Primary Examiner* — Melanie Y Brown
*Assistant Examiner* — Erik B Crawford
(74) *Attorney, Agent, or Firm* — Foley Hoag LLP

(57) ABSTRACT

Disclosed is a method for determining the presence and/or amount Oran analyte of interest in a liquid sample comprising the steps of: contacting the liquid sample suspected of containing analyte with a gas generating means (eg. catalase and peracid or peroxygen compound), which gas generating means forms a gas dependent upon the presence, absence or amount of analyte, which gas creates one or more bubbles in the liquid sample which act to alter the flow of liquid along a flow path; and determining an alteration of flow in the liquid wherein the alteration of flow of liquid along the flow path is indicative of the presence and/or amount of analyte in the liquid sample.

12 Claims, 14 Drawing Sheets

(51) Int. Cl.
 *B01L 3/00* (2006.01)
 *G01N 33/58* (2006.01)
(52) U.S. Cl.
 CPC .... *B01L 2300/025* (2013.01); *B01L 2300/0816* (2013.01); *B01L 2400/046* (2013.01); *B01L 2400/0406* (2013.01); *B01L 2400/0622* (2013.01); *G01N 2333/59* (2013.01); *G01N 2333/908* (2013.01)

(56) References Cited

U.S. PATENT DOCUMENTS

| 4,713,347 | A | 12/1987 | Mitchell et al. |
| 4,791,060 | A | 12/1988 | Chandler |
| 5,087,556 | A | 2/1992 | Ertinghausen |
| 2007/0248953 | A1 | 10/2007 | Sand |

\* cited by examiner

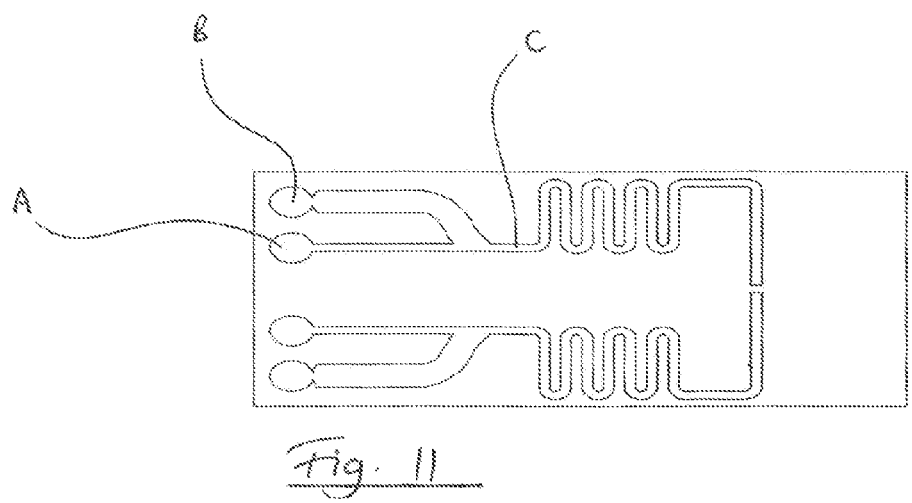
Fig. 11
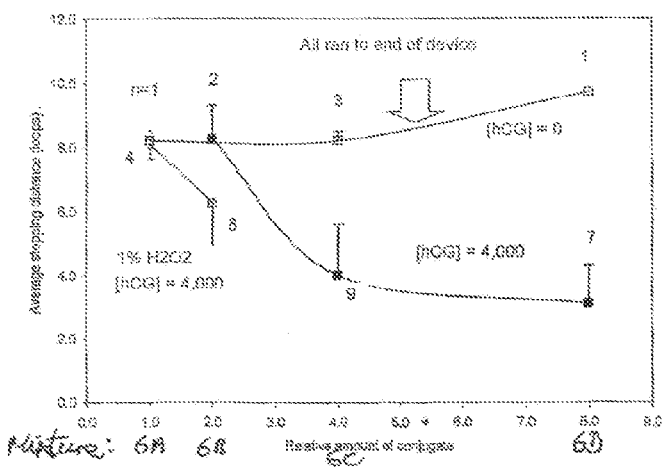
Figure 12: Cessation of flow in a capillary channel as a function of [hCG], 3299-catalase and [H₂O₂].

ASSAY DEVICE COMPRISING BUBBLE-FORMING MEANS

This application is a 371 national stage application of PCT/GB2009/050354, filed Apr. 9, 2009, which claims priority to GB 0806771.2, filed Apr. 12, 2008 and GB 0821552.7, filed Nov. 26, 2008. The entire contents of each of these applications are hereby incorporated by reference.

FIELD OF THE INVENTION

The present invention relates to an assay device, a method of controlling the flow of a liquid along an assay device during performance of an assay, a method of performing an assay using the assay device, and a method of making an assay device.

BACKGROUND OF THE INVENTION

Cheap, disposable assay devices e.g. of the sort routinely used at home or point-of-care, tend to fall into one of two types: lateral flow assay devices, and micro fluidics devices.

Lateral flow assay devices such as disclosed by EP291194, are those of the type in which a liquid sample is applied, directly or (more usually) indirectly, to a porous matrix, such as a nitrocellulose or paper filter. The liquid sample migrates along the porous matrix, generally mobilising a dried assay reagent or component (typically a labelled antibody such as a particulate labelled antibody) releasably immobilised on the porous matrix. Typically the labelled antibody forms a complex with the analyte of interest in the sample, which labelled complex is usually then captured in a detection region of the porous matrix, by a second antibody for the analyte of interest. Accumulation of the labelled binding reagent in the detection region or zone is therefore indicative of the presence, absence or extent of analyte in a liquid sample. It will be appreciated that other variants of lateral flow assays exist, in particular competition format assays in which a labelled reagent tends to be captured in the detection zone if the analyte is not present in the sample. Lateral flow assay devices are routinely used for example to determine the presence or absence of the pregnancy hormone hCG and to provide the user with an indication of either being pregnant or not pregnant.

Detection of labelled reagent at the detection zone may be carried out visually or by means a photodetector. Visual read non electronic assay devices have the advantage of being low cost, however a problem associated with such assay devices, especially pregnancy-testing devices and/or home-use assay devices, is that they provide an assay result as a signal of variable strength, which can require a degree of interpretation. This leaves the assay result open to misinterpretation, especially where the user or reader of the assay device has a preferred assay result in mind. These tests are often provided as threshold tests, with levels of labelled reagent below the threshold, in the case of a sandwich assay, indicating a negative result and levels of labelled reagent above the threshold indicating a positive result. As a consequence, electronic digital devices have been developed wherein the presence or amount of the labelled reagent is determined by means of a photodetector and the result of the assay displayed on an LCD display. Such digital devices have the advantage in that they provide an unambiguous result such as "YES" or "NO" which does not require interpretation. Such devices may be single use and therefore disposable. They are however expensive to produce as they typically require one or more photodetectors, one or more light sources such as an LED, a power source, an electronic circuit and a digital display. Furthermore the disposal of electronic devices has environmental issues.

In a microfluidics assay device, many of the same principles as used in a lateral flow assay may be employed. However, instead of the liquid sample being applied to a porous matrix, the sample is applied or fed into a conduit or channel, along which the liquid advances, usually by means of capillary action. A detection zone may be provided on an inner surface of the channel on which for example an immobilised binding reagent is provided. Micro fluidic devices have particular advantages in that the flow path is well defined and the device may be engineered to incorporate microfabricated elements such as bifurcations, mixing regions, flow control elements, time gates, filters and so on. Examples of microfluidic assay devices are described in U.S. Pat. No. 5,458,852.

Assay devices for measuring an analyte wherein the rate of flow of a liquid along a flow path is indicative of the presence or extent of an analyte are known.

U.S. Pat. No. 4,963,498 discloses a micro fluidic device for the measurement of an analyte in, or a property of a fluid sample wherein reagents present in the device affect the flow rate of the sample. The device may comprise both a test capillary and a reference or control capillary.

EP456699 discloses an apparatus for testing the presence of a substance in a liquid comprising a sample application port connected to a number of fluid conduits upstream from respective indicator chambers. According to an example, agglutination reagents present in the fluid conduits interact with the sample in order to change its flow rate, for example, preventing the liquid from reaching an indicator chamber within the time frame of the assay.

A capillary device for testing for the presence of a substance is also disclosed by WO2004/083859. The device works by causing agglutination of a liquid sample in a test capillary in the presence of an analyte of interest (typically, human chorionic gonadotropin, hCG), which agglutination prevents the flow of liquid sample in the test capillary but not in a control capillary (which contains no agglutination reagents). The presence or absence of liquid sample at downstream portions of the test and control capillaries is detected by electrodes.

It is also known (e.g. from WO 2006/090144) to provide microfluidics assay devices in which a flow path is formed with a discontinuity therein, e.g. in the form of a portion of a flow path channel having an orifice or aperture too large to be bridged by the advancing liquid sample; and wherein the orifice or aperture can be filled by the same or another liquid (e.g. having flowed along a second flow path), thereby acting as a "bridge" allowing the liquid sample to advance past the discontinuity. This arrangement can form the basis of a "binary assay device", in which the presence or absence of the analyte of interest in a sample influences the rate of advance of the liquid sample along one or more different flow paths within an assay device, which in turn can determine whether a liquid flowing along a particular one of the flow paths enters an 'indicator' region of the assay device, thereby indicating in simple qualitative terms (e.g. "yes" or "no") the result of the assay, thus removing any element of subjectivity about interpretation of the assay result without the need for sophisticated electronics or other display means.

A variant of the arrangement described above is disclosed in WO2008/025945, in which there is a "race" between liquid flowing along a 'test' flow path and a liquid flowing along a reference flow path. There is a junction region in which the test and reference flow paths contact one another. If the liquid flowing along the reference flow path "wins the race" and reaches the junction region before the liquid flowing along the test flow path, then the further flow of liquid along the test flow path is prevented.

SUMMARY OF THE INVENTION

In a first aspect the invention provides a method for determining the presence and/or amount of an analyte of interest in a liquid sample comprising the steps of: contacting the liquid sample suspected of containing analyte with a gas generating means, which gas generating means forms a gas dependent upon the presence, absence or amount of analyte, which gas creates one or more bubbles in the liquid sample which act to alter the flow of liquid along a flow path; and determining an alteration of flow in the liquid wherein the alteration of flow of liquid along the flow path is indicative of the presence and/or amount of analyte in the liquid sample.

A determination of an alteration of flow may include determining an outcome as a consequence of an alteration in flow of liquid. Such an outcome may be for example an indication that liquid has arrived a particular zone.

The liquid in which an alteration of flow is determined may be the liquid sample itself. Alternatively it may be a second liquid wherein the liquid sample is fluidically connected to the second liquid such that generation of one or more gas bubbles in the liquid sample causes an alteration of flow in the second liquid. The second liquid may be applied to a device in which the method may be carried out in or may comprise part of the device.

In a second aspect the invention provides a method of determining the presence and/or amount of an analyte in a liquid sample, comprising the steps of:
  a) contacting the liquid sample suspected of containing analyte with a binding reagent labelled with a first reagent, wherein the binding reagent is capable of binding to the analyte or to a binding reagent for the analyte;
  b) causing the accumulation at an accumulation zone of the labelled binding reagent, wherein accumulation of labelled reagent at the accumulation zone is dependent upon the presence, absence or amount of analyte in the liquid sample; and
  c) contacting the labelled binding reagent at the accumulation zone with a second reagent such that first and second reagents react to form a gas, which gas creates one or more bubbles in the liquid sample, which acts to alter the flow of liquid along a flow path, wherein the altering of flow of liquid along said flow path is indicative of the presence and/or amount of an analyte in the liquid sample.

It is an object of the invention to provide a relatively inexpensive assay device which, in preferred embodiments, is able to provide an unequivocal or "binary" or digital outcome of the determination of an analyte in a liquid sample wherein the assay device has no or few electronic components. In an embodiment, the invention is able to provide an assay device which is capable of providing an optically detectable binary or digital result of an assay, wherein the assay device does not comprise elements which require a power source or a power source per se. Elements include one or more of: a photodiode, a photodetector, an electronic display and an electronic circuit. Preferably the result is visually detectable by the naked eye.

According to a third aspect, the invention provides an assay device for determining the presence and/or amount of an analyte of interest in a liquid sample applied, or otherwise introduced, to the device, the device comprising:

at least one assay flow path along which a liquid flows;
a gas generating means which generates a gas dependent upon the presence, absence or amount of analyte, which gas creates one or more bubbles in the liquid sample which acts to alter the flow of liquid along the flow path to a downstream zone; and
a detection means to detect any alteration in flow of liquid and/or an indicator region to detect the presence or arrival of liquid at the downstream zone; wherein the altering of flow of liquid along the flow path is indicative of the presence and/or amount of an analyte.

The gas generating means may comprise a first reagent which when in contact with a suitable second reagent, causes or otherwise participates in a reaction which generates, directly or indirectly, a gaseous product. The assay device will typically comprise at least one of the reagents required in a reaction between two or more reagents, which reaction has, as a direct or indirect product, the formation of a gas. Preferably the assay device will comprise all of the reagents necessary for the gas-producing reaction to take place. The reagents may comprise, for example, two or more reactants, or at least one reactant and a catalyst (such as an enzyme) which catalyses the conversion of the reactant or reactants into a gaseous product.

The formation of one or more bubbles tends to inhibit the flow of liquid along the flow path, typically in the region in which the one or more bubbles are located or downstream from the one or more bubbles. Flow along the flow path may be stopped by the formation of one or more bubbles. Alternatively, the formation of bubbles may increase the rate of flow of liquid along the flowpath.

In a fourth aspect, the invention provides an assay device for determining the presence and/or amount of an analyte of interest in a liquid sample, the device comprising:
  a) sample application zone for application of liquid sample to the device;
  b) at least one assay flow path along which a liquid flows;
  c) a binding reagent labelled with a first reagent and provided upstream from an accumulation zone provided within said flow path, said binding reagent being capable of binding either to the analyte or to a binding reagent for the analyte;
  d) an accumulation zone capable of immobilising the labelled binding reagent wherein accumulation of labelled reagent at the accumulation zone is dependent upon the presence, absence or amount of analyte in the liquid sample; the device being such that, in use, a reaction occurs between any immobilised labelled binding reagent at the accumulation zone and a second reagent to produce a gas, said gas forming one or more bubbles in the liquid sample, which bubbles act to alter the flow of liquid along the flow path, wherein the altering of flow of liquid is indicative of the presence or amount of analyte in the liquid sample; and
  e) a detection means to detect any alteration in flow of the liquid and/or an indicator region provided downstream of the accumulation zone to detect the presence or arrival of liquid.

Labelled binding reagent may be accumulated at the accumulation zone in an analyte dependent manner. Analyte present in the liquid may form an analyte—binding reagent complex with the labelled binding reagent which may be subsequently accumulated at the accumulation zone.

A second binding reagent for the analyte may be provided in an immobilised form at the accumulation zone in order to capture the analyte—labelled binding reagent complex. Alternatively or additionally, analyte may be captured at the accumulation zone by the immobilised second binding reagent prior to formation of a complex with the labelled binding reagent.

Yet alternatively the second binding reagent may be provided in a mobilisable form which is capable of being immobilised at the accumulation zone. For example the accumulation zone may be labelled with binding reagent such as biotin and the second binding reagent for the analyte labelled with a complementary binding partner for the binding reagent at the accumulation zone, such as streptavidin.

In a further embodiment, the second binding reagent for the analyte may be attached to a magnetic particle. A magnet may be provided in the vicinity of the accumulation zone in order to immobilise the magnetically labelled second binding reagent. Any first binding reagent/analyte/second binding reagent complex formed may, for example, be moved into the accumulation zone by means of a magnet.

Yet alternatively, the accumulation zone may comprise a size exclusion filter wherein the second binding reagent is unable to pass through the filter. The second binding reagent may for example be attached to a particle whose diameter is larger than that of the average pore diameter of the pores in the filter. Thus any first labelled binding reagent/analyte/second binding reagent complex is retained at the filter whereas uncomplexed labelled binding reagent is able to pass through it.

Determination of the analyte may be carried out by means of a competition or inhibition type reaction. The labelled binding reagent may comprise a labelled analyte or analyte analogue. This method is suitable for the detection of small analytes, such as haptens. For example, an analyte or analyte analogue may be immobilised at the accumulation zone which may serve to capture the labelled binding reagent. Alternatively a binding reagent for the analyte may be provided at the accumulation zone and a labelled analyte or analyte analogue provided upstream from the accumulation zone which competes with any analyte present for the binding reagent at the accumulation zone.

The labelled binding reagent may be provided at the accumulation zone instead of or in addition to being provided upstream from the accumulation zone.

The device may further comprise a second reagent provided upstream from the accumulation zone such that in use, all or substantially all of the labelled binding reagent is transported to the accumulation zone prior to the arrival of second reagent at said zone.

According to a fifth aspect, the invention provides an assay device for determining the presence and/or amount of an analyte of interest in a liquid sample, the device comprising:

a) a sample application zone for application of liquid sample to the device;

b) at least one assay flow path along which a liquid flows;

c) a binding reagent labelled with a first reagent and provided upstream from an accumulation zone provided within said flow-path, said binding reagent being capable of binding either to the analyte or to a binding reagent for the analyte;

d) a second reagent provided upstream of said accumulation zone; and e) an accumulation zone capable of immobilising the labelled binding reagent wherein accumulation of labelled reagent at the accumulation zone is dependent upon the presence, absence or amount of analyte in the liquid sample; the device being such that, in use, all or substantially all of the labelled binding reagent is transported to the accumulation zone prior to the arrival of second reagent at said zone, whereupon the arrival of the second reagent at the accumulation zone results in a reaction between any immobilised labelled binding reagent at the accumulation zone and the second reagent to produce a gas, said gas forming one or more bubbles in a liquid, which bubbles act to alter the flow of liquid along the flow path, wherein the altering of flow of liquid is indicative of the presence and/or amount of analyte in the liquid sample.

The second reagent may be provided in a separate flow path to the first reagent. The assay device may comprise two flow paths wherein the first reagent is provided in a first flow path and the second reagent is provided in a second flow path. The first and second flow paths may converge at an intersection, at or upstream from, the accumulation zone. The first and second flow paths may be provided such that the time taken for labelled binding reagent to reach the accumulation zone is less than the time taken for second reagent to reach said zone. There are many different ways to achieve this. The two flow paths may, for example, differ from each other in their respective lengths, widths, surface coatings or combinations thereof. One of the flow paths may provided with one or more flow restriction or flow promotion elements, and so on, such that the second reagent arrives at the accumulation zone after all of, or after substantially all of, the labelled binding reagent.

In use, liquid sample applied to the device will resuspend the first and second reagents provided respectively in the first and second flow paths and, depending upon the extent of analyte present, result in the accumulation of labelled binding reagent at the accumulation zone. Due to the differences between the first and second flow paths, all or substantially all of the labelled binding reagent will arrive at the accumulation zone prior to the arrival of second reagent. Any labelled binding reagent not accumulated at the accumulation zone will pass downstream along with liquid sample. Thus formation of one or more gas bubbles at the accumulation zone will be principally due to reaction between the second reagent and any first reagent accumulated at the accumulation zone and thus indicative of the presence and/or amount of analyte present.

The intersection between the first and second flow paths enables the two streams of fluid from the separate flow paths to be brought together into a single flow path. Preferably the intersection is designed so as not to introduce an air lock which may impede the passage of liquid from either flow path downstream of the intersection.

The assay device may comprise a common sample application region that connects the first and second flow paths. Thus a single liquid sample applied or otherwise introduced to the assay device will be able to flow along both the first and second flow paths simultaneously.

Other ways to deliver the first and second reagents sequentially to the accumulation zone may be envisaged. For example, the assay device may comprise a sample application zone located part way along a flow path such that liquid sample applied to the device flows in two directions, respectively away and towards the accumulation zone. First and second reagents may be provided in the device such that liquid sample flowing away from the accumulation zone mobilises the second reagent and liquid sample flowing towards the accumulation zone mobilises the first reagent. The assay device may comprise a liquid sink which when contacted by liquid sample, typically the portion that comprises the first reagent, is capable of pulling all of the liquid sample applied to the device towards the accumulation zone. Thus in use, all or substantially all of the first reagent may arrive at the accumulation zone prior to the arrival of second reagent.

The device may comprise a means to determine the alteration of the flow of liquid, Determining an alteration in flow may be carried out by measuring the flow rate of the liquid. The alteration of flow may be determined with respect to one or more flow rate thresholds.

The assay device may comprise a means to detect the presence of liquid sample in the flow path, for example downstream of the accumulation zone. For example the assay device may comprise one more electrode pairs to detect the presence of liquid sample. A rate of flow between respective electrode pairs may be determined This may be achieved for example by provision of a plurality of electrode pairs at one or more spaced intervals, each electrode pair being able to determine the presence of liquid sample. The assay device may further comprise a simple timer in order to record the time taken for the liquid sample to travel along the flow path.

Determination of the alteration in flow may also be carried out by comparing the flow of liquid in the assay flow path, which for the sake of convenience may also be referred to as the "test" flow path, relative to the flow of liquid in a reference flow path.

The assay device may comprise one or more indicator regions to indicate the arrival of liquid at one or more downstream zones. The indicator region is preferably visually detectable and may comprise for example a colour change means such as a chemical which reacts with the liquid to produce a colour. The colour change means may be immobilised in the flow path or may for example comprise a dried coloured dye which is dissolvable in the liquid.

The colour change means may be sensitive to pH. The indicator region is typically provided downstream of the accumulation zone. The indicator region may for example may comprise a chamber into which liquid may enter and through which liquid may pass. The chamber may be provided at the end of a flow path such that fluid enters the chamber and ceases to flow any further.

The assay device may further comprise a reference flow path wherein flow of liquid along the reference path is compared to flow of liquid along the assay flow path. The reference flow path may be free from any reagents that are capable of generating gas.

The assay device may comprise two indicator regions provided respectively downstream from the accumulation zone of the test flow path and towards or at the distal end of the reference flow path. A common sample application zone may connect the assay and reference flow paths such that a liquid sample applied to the device is able to flow along the respective flow paths.

The test and reference flow paths may each comprise an indicator region. The indication regions may differ from each other so as to provide a visually different result. For example the indicator regions of the respective test and reference flow paths may generate different colours due to the provision of different colour change means. Alternatively the two indicator regions may indicate words or symbols reflecting for example "positive" or "negative".

The flow of liquid may be altered by reducing or stopping the flow of liquid or a portion thereof. Alternatively the flow of liquid may be altered by increasing or restarting the flow of liquid or a portion thereof.

Surprisingly the inventors have found that gas bubbles are generated only to a significant extent when the second reagent contacts a relatively concentrated amount of the immobilised labelled binding reagent at the accumulation zone. By optimising the amounts of labelled binding reagent and second reagent, the fluidic dimensions of the device and the relative positions of the labelled binding reagent and second reagent within the device, any reaction between the second reagent and non-immobilised binding reagent may be kept to a minimum and is not necessarily detrimental to the performance of the assay.

In a sixth aspect the invention provides an assay kit for determining the presence and/or amount of an analyte in a liquid sample, comprising:
a) an assay device comprising a flow path in which is provided an accumulation capable of immobilising a labelled binding reagent;
b) binding reagent labelled with a first reagent; and
c) a second reagent which is capable of reacting with the first reagent at the accumulation zone to produce a gas, said gas forming one or more bubbles in a liquid, which bubbles act alter the flow of liquid along the flow path, wherein the altering of flow of liquid is indicative of the presence or amount of analyte in the liquid sample.

In a seventh aspect the invention provides a method of altering the flow of a liquid sample along a flow path, comprising the steps of
a) applying the sample to the flow path thereby accumulating a first reagent at an accumulation zone provided within the flow path; and
b) thereafter contacting the immobilised reagent with a second reagent such that first and second reagents react to form a gas, which gas creates one or more bubbles in a liquid which acts to alter the flow of liquid along the flow path.

The method according to the seventh aspect may further comprise the step of detecting or determining any alteration in flow of the liquid sample.

In an eighth aspect, the invention provides a device for detecting an alteration of flow of a liquid sample along a flow path, comprising:
a) a sample application zone for application of liquid sample to the device;
b) at least a flow path along which a liquid flows;
c) a first reagent provided upstream from an accumulation zone;
d) an accumulation zone capable of accumulating the first reagent; the device being such that, in use, a reaction occurs between accumulated first reagent at the accumulation zone and a second reagent to produce a gas, said gas forming one or more bubbles in a liquid, which bubbles act alter the flow of liquid along the flow path; and
e) a detection means to detect any alteration in flow of the liquid sample and/or an indicator region provided downstream of the accumulation zone to detect the presence or arrival of liquid.

The device according to the eighth aspect may further comprise a second reagent provided upstream from the accumulation zone such that in use, all of substantially all of the first reagent is transported to the accumulation zone prior to the arrival of second reagent at said zone.

The one or more flow paths may comprise or consist of a micro fluidic channel, a porous matrix (such as a chromatographic membrane), or a combination of the two. Preferred porous matrices include nitrocellulose and filter paper. The microfluidic channel is preferably of capillary dimensions, such that the liquid sample is able to advance along the channel by capillary flow. Typical micro fluidic channels have an internal cross-sectional dimension of between 0.1 and 500 µm, more typically between 1 and 100 µm. The microfluidic channel or channels may be formed, for example, from synthetic plastics materials such as polycarbonate, polyester, epoxy resin, or glass or metal. The channel or channels may formed by etching, casting, moulding etc. using conventional techniques.

A device may comprise a microfluidic channel having a typical width of 1 mm and a typical height of 100 um. The device may comprise a number of laminates such as, a lower base layer, an intermediate layer comprising the channel structures and an upper layer which serves to seal the microfluidic channel(s).

The analyte of interest may comprise, for example, a steroid, a hormone, a peptide or polypeptide, a carbohydrate, a lipid, a protein, a lipoprotein, a polynucleotide, an enzyme, a blood group marker, a disease marker, a diagnostic or prognostic indicator, a cation, an anion, or a molecular complex such as a virus, bacterium, yeast, fungus, spore or eukaryotic cell. In one preferred embodiment the analyte of interest comprises hCG. In another embodiment, the analyte is glucose. The assay device according to the invention is suitable for the detection of analytes including small molecules such as haptens. Haptens may be defined as small antigenic determinants capable of eliciting an immune response only when coupled to a carrier. Haptens bind to antibodies but by themselves cannot elicit an antibody response, for example by injection of the hapten into the body of an animal. Non-limiting examples of haptens include amphetamine based drugs of abuse such as MDA (3,4-methylenedioxyamphetamine), MDMA also known as "Ecstasy" (3,4-methylenedioxy-N-methylamphetamine), MDEA (3,4-methylenedioxy-N-ethylamphetamine), BDB (3,4-methylenedioxyphenyl-2-butanamine), MBDB (3,4-methylenedioxyphenyl-N-methylbutanamine), and MDPA (3,4-methylenedioxy-N-propylamphetamine); opiates such as morphine and codeine, as well as their synthetic analogues which includes heroin, hydromorphone, hydrocodone, oxycodone and oxymorphone; lysergic acid diethylamide (LSD) as well as metabolites thereof; tetrahydrocannabinol and cocaine; toxic drugs such as diazepam, nicotine, acetaminophen, caffeine, risperidone, phenobarbitol; hormones such as progesterone, estradiol and metabolites thereof, testosterone; pesticides; dyes such as fluorescein isothiocyanate, Texas red and so on.

The liquid sample may be any suitable liquid, such as water, sewage sample, or an aqueous extract (e.g. an aqueous food or drink sample) or a biological sample e.g. blood, plasma, serum, urine, pus, sweat, saliva, vaginal fluid, or tears. A preferred sample is urine. The liquid sample may be applied to the device 'neat' or may be subjected to a pre-treatment step (e.g. including one or more of the following: mixing; agitation; sonication; dilution; incubation; denaturation; or reaction with one or more reagents).

The liquid in which the bubble or bubbles form may conveniently be the sample liquid, substantially as applied to the device (but allowing for any alteration of the composition of the liquid as a result of contact with the assay device e.g. the resuspension or dissolution in the sample liquid of a reagent or other substance deposited or otherwise provided in the flow path of the assay device). Alternatively, or additionally, the bubble or bubbles may be formed in some other liquid, such as a buffer wash liquid or additional reagent solution separately applied to the assay device. In either event the liquid will generally be aqueous (i.e. over 50% v/v $H_2O$).

It will be understood that the gas formed by the reagent or reagents must be at least partially insoluble in the liquid, under the conditions of temperature and pressure in which the assay is performed, for the duration of time over which the flow of liquid is to be prevented or reduced. Normally the assay will be performed at room temperature (i.e. about 18-25° C.), but the assay could be performed in a cold room or refrigerator (at about 3-6° C.) or could be performed in an incubator (at a temperature from about 25° C. to about 40° C.). Typically the assay will be performed at atmospheric pressure (generally this will be in the region 970 millibars to about 1030 millibars at sea level). Accordingly, the concentration of gas formed must be above the solubility of the gas in the relevant liquid, for at least a portion of the time taken to perform the assay. Gases which have low levels of solubility in the liquid sample, such as oxygen, are preferred.

Within the foregoing constraints, the gas used to form the gas bubble may be any suitable gas, although obviously highly toxic or highly reactive materials are less preferred. Suitable gases may include, but are not limited to, oxygen, ozone, carbon dioxide, carbon monoxide, methane, ethane, nitrogen, nitrogen oxides, hydrogen, helium, noble gases, or any combination of any two or more of the foregoing. Generally preferred gases include oxygen, carbon dioxide, nitrogen and hydrogen.

The first reagent is one which is able to react with the second reagent to generate a gas. The first and/or second reagents may be provided to the assay device as part of the sample liquid, or as a separate addition of a liquid to the assay device, or more preferably will form an integral component of the assay device e.g. deposited on or in the assay device, typically on or in one or more flow paths, in dried or freeze dried form). The first reagent may be an enzyme.

Suitable enzymes for use as a first reagent include oxoreductases such as catalase or glucose oxidase. Catalase (EC 1.11.1.6) catalyses the degradation of hydrogen peroxide to water and oxygen. This reaction is useful since, apart from generating the necessary gas (in this instance, oxygen), the only other product is water, which will have no significant effect on the performance of the assay or its result. Catalase is widely available commercially in high purity and can be lyophilised. Another advantage of using a catalase-based gas generation system is that only a single further reagent, such as hydrogen peroxide, is required. Thus, in order to generate gas it is necessary only to contact hydrogen peroxide with an enzymatically active amount of catalase.

In the case where the first reagent is an oxoreductase such as catalase, the second reagent may comprise a source of oxygen gas. Examples of sources of oxygen gas are peroxygens or peracids such as hydrogen peroxide, carbamide peroxide, alkali metal peroxides, urea hydrogen peroxide, alkali metal carbonates alkali metal perborates, and alkali metal percarbonates. A solid source of oxygen such as urea hydrogen peroxide has the advantage in that it may be provided as part of the assay device in the dry state.

Glucose oxidase (E.C. 1.1.3.4) catalyses the oxidation of β-D-glucose to D-glucono-1,5-lactone with the co-formation of hydrogen peroxide. Thus, this system can be used for the in situ generation of hydrogen peroxide in the assay device, which can then be acted on by a catalase. Thus, in one embodiment the assay device of the invention may comprise both a glucose oxidase and a catalase. Glucose may be readily provided as a dried deposit on the assay device, which is readily rehydrated and dissolved by sample liquid. Small amounts of oxygen may be present in the assay device (either dissolved in the sample liquid or present in air in the flow path ahead of the advancing liquid), which should be sufficient to react with the glucose to form hydrogen peroxide, which in turn is converted into oxygen by a catalase.

Other gas generating enzymes that may be used include those which generate carbon dioxide such as dehydrogenases and decarboxylases, for example pyruvate dehydrogenase, isocitrate dehydrogenase, amino-acid decarboxylase, oxalate decarboxylase, pyruvate decarboxylase, and urease, the latter capable of catalysing the hydrolysis of urea into carbon dioxide and ammonia.

The binding reagent may be one which has a binding affinity for the analyte of interest and forms a binding pair. Binding pairs are well-known to those skilled in the art and include antibody-antigen, ligand/receptor, complementary oligo- or polynucleotides, or other pairs of molecules that bind to one another. The binding reagent may be an antibody to the analyte of interest. The binding reagent may be an analyte or analyte analogue.

Conveniently the binding reagent is an immunoglobulin molecule or an antigen-binding portion of such a molecule, which term is intended to encompass scFv, Fab, Fab', $F(ab')_2$, single domain antibodies, multimers of any of these, and the like. Methods of cross-linking or attaching immunoglobulins (or portions thereof) to other molecules are well-established. In particular it is well-known to those skilled in the art to attach immunoglobulins (or portions thereof) to other polypeptides such as enzymes. In some embodiments of the present invention, the assay device/method comprises an immunoglobulin molecule (or an antigen-binding portion thereof or a multimer of immunoglobulins or antigen-binding portions thereof), attached to an enzyme, especially an enzyme which catalyses a gas-forming reaction.

The binding reagent may be attached to the first reagent which participates in, or catalyses, the gas-forming reaction. Desirably the binding partner, such as an immunoglobulin molecule or other binding partner (or antigen-binding portion thereof) is attached to an enzyme, such as catalase, for example. Alternatively the labelled binding reagent may be formed in-situ by binding of the first reagent to the binding partner.

Application of a liquid (preferably sample liquid) to a liquid application region (e.g. a sample application zone or port) causes liquid to flow (preferably by capillary action) along a flow path in the assay device. Entrained within the flowing liquid (e.g. either contained within the liquid applied to the device, or already present in the device and mobilised by contact with the liquid) is a first reagent which participates in a gas-forming reaction when contacted or mixed with a second reagent.

The assay device may comprise a non electronic, binary or digital assay result generation and/or indicator region, namely it does not require a power source in order to generate and/or display the result of the assay. Preferably the assay device comprises no electronic components whatsoever. A binary or digital result is one wherein the result given is unambiguous. It may be a single answer given from two possible outcomes, for example "positive or "negative", "yes" or "no", greater or less than a threshold value and so on. It may be a single answer given from more than two possible outcomes. The result may be provided with respect to a threshold. Thus a positive result may be given for a level of analyte which is higher than a particular threshold value A binary or digital result is distinct from, for example a visually read result from a visual read lateral flow assay device, such as the ClearBlue™ pregnancy device, wherein the result is dependent upon the colour intensity of a test line and is therefore subject to interpretation by the user.

Binary or digital assays are disclosed in WO 2008/025945 and WO 2006/090144 and are hereby incorporated by reference. Binary assays are further illustrated in FIG. 8 and described in further detail below.

A reference flow path where provided will typically be free from any gas generating reagents.

The assay device may comprise a test flow path and a reference flow path which intersect at a junction region downstream from the accumulation zone. The junction region may also comprise an outlet, conduit, chamber or other portion which permits the onward flow of liquid.

The junction region may only allow for the onward passage of either the liquid in the test flow path or the liquid in the reference flow path. The junction region may comprise a fluid valve or choke such that liquid flowing along the reference flow path, upon reaching the junction region, has the effect of preventing the flow of liquid along the test flow path or vice-versa. Thus detection of liquid or downstream of the junction zone is indicative of either liquid from the reference flow path or the test flow path.

The test or reference flow paths may converge at a junction region which permits the onward flow of a liquid contained within a reservoir into one of two indicator regions, one operably associated with the reference flow path and the other operably associated with the test flow path. The reservoir liquid will flow into one of these indicator regions depending upon whether liquid from the test flow path or from the reference flow path reaches the junction first.

A junction region is useful when it is necessary to arrest flow of one flow channel by the other or provide for further onward flow of a reservoir channel. However in some circumstances flow in the test channel may be completely stopped within the time of the test or flow may be arrested to such an extent that liquid in the test channel does not reach the junction and therefore a junction region may not be an essential requirement. However, a junction region is preferred in a number of embodiments.

In some embodiments it may be preferred to bias the assay device so as to avoid liquid from the reference and test flow paths arriving at the junction region simultaneously. This may be achieved by providing reference and test flow paths of differing widths, differing lengths and so on. The assay device may be biased such that in the absence of gas generation in the test flow path, liquid arrives at the junction region from the test flow path prior to the arrival of liquid from the reference flow path or vice versa. The device may be adapted to provide a positive or negative result with respect to a threshold value. Thus for a sandwich type assay, in the presence of analyte below a certain threshold, and therefore in the presence of some gas generation, liquid from the test flow path may arrive at the junction region prior to the arrival of liquid from the reference flow path or vice versa.

One or more indicator regions may be provided upstream or downstream of the junction region.

According to an embodiment, the assay device may comprise an indicator region provided downstream of the junction region which is able to indicate which of the liquids from the test or reference flow paths reached the junction region first. There are a great many ways by which a colour change in this indicator region may be effected.

For example a coloured dye may be provided in either the test or reference flow path or dyes of different colours may be provided in the respective test and reference flow paths, such that the presence of a dye of a particular colour in the indicator region reveals by which route (the test or reference flow path) liquid first reached the indicator region. Alternatively, the indicator region may comprise a first reactant and second reactant may be provided in one of the flow paths, such that first and second reactants react to produce a colour change. Different reactants may be provided in the test and reference flow paths which are capable of reacting with a reactant in the indicator region to provided different colour changes such that the resulting colour would differ depending upon whether onward flow of the liquid from the test flow path or reference flow path occurred. In a further example, two different enzymes (e.g. horseradish peroxidase and glucose oxidase) may be provided in the indicator region, and a respective substrate for one of the enzymes could be provided in one of the flow paths which reacts, in the presence of the relevant enzyme catalyst, to produce a coloured product. The colour of the product reveals which substrate was introduced into the indicator region (and hence by which flow path liquid first arrived there). In general terms, the indicator region (if located downstream of the junction region) may comprise components of two different signal-generating means which generate detectably different signals, with one or more further components of each signal-generating means being mobilisably disposed upstream, the further component of one signal-generating means being disposed in the test flow path, and the further component of the other signal-generating means being disposed in the reference flow path, the further component being required to contact the other component in the indicator region in order to generate a signal. Which of the two signal-generating means is activated depends on which of the further components reaches the indicator region first, which in turn depends on the relative rates of flow of liquid along the test and reference flow paths.

In an embodiment, the indicator region comprises a pH-sensitive indicator, and the test and reference flow paths each comprise a different pH-affecting agent e.g. one comprises a buffer at relatively acidic pH and one comprises a buffer at relatively alkaline pH. The flow path by which liquid first reaches the indicator region will therefore determine the pH in the indicator region and hence the colour of the indicator. The indicator provided in an indicator region may be provided in an immobilised form for example on the surface of a channel or on or within a porous matrix such as paper provided in an indicator region.

Embodiments of this general type, with a downstream indicator region, have the advantage that it may not be necessary to alter the flow of liquid along the test flow path by a large amount in order for the liquid flowing along the reference flow path to reach the indicator region first, or vice-versa,—a time differential of as little as 1 or 2 seconds may suffice.

In other embodiments an indicator region is provided, upstream of the junction region, in each of the reference and the test flow paths. In an embodiment, flow of liquid along the reference flow path to a certain point acts to block flow of liquid along the test flow path before the liquid reaches the indicator region on the test flow path, such that a certain assay result is displayed in the indicator region. In some embodiments it may be advantageous to provide an indicator substance, such as a dye, upstream of the indicator region, such that a visible change can be seen if/when liquid reaches the indicator region of the test and/or reference flow paths.

According to an embodiment, the assay device comprises indicator regions provided in both the test and reference flow paths upstream from the junction region. In the presence of analyte, which for a sandwich type assay will result in the generation of one or more gas bubbles, flow along the test flow path slows or ceases, enabling liquid from the reference flow path to reach its indicator region first and indicate the presence of analyte. In the absence of analyte, the test and reference flow paths may be configured such that liquid sample from the test flow path reaches the junction region before liquid from the reference flow path. Once liquid from the test flow path reaches the junction region it blocks off flow in the reference flow path such that liquid in reference path never reaches, at least within the time of the test, the reference indicator region.

In some embodiments, the indicator region comprises a microfluidic channel, such as a capillary, which is visible to a user (e.g. through a window or aperture in an otherwise opaque housing). In one embodiment the indicator region comprises two channels or capillaries, one forming part of the test flow path and one forming part of the reference flow path. In one embodiment, the microfluidic channels or capillaries in the indicator region become filled with a coloured liquid during performance of the assay. The colour of the liquid may itself indicate the result of the assay. Alternatively, the coloured liquid may simply serve to alter the visibility of the channel or capillary. For example, a clear plastics or glass capillary against a clear or white background may not be readily apparent. Introduction of a coloured liquid into such a channel or capillary will increase contrast and render the channel or capillary readily visible. Alternatively, if the channel or capillary is initially of high contrast with its background (e.g. a white capillary against a red background), then introduction of a coloured liquid into the channel or capillary which is of the same colour as the background will reduce the contrast and render the capillary or channel difficult to observe. These all represent different methods of conveying or displaying a visible signal concerning the outcome of the assay.

In some embodiments, the indicator region may comprise one or more channels or capillaries which form one or more words or symbols (such as "PREGNANT", or a plus or minus symbol). In one particular embodiment, in which an assay device in accordance with the invention is provided as a pregnancy test device, one flow path comprises an indicator region in which a channel or capillary forms the word "NOT", and another flow path comprises an indicator region in which a channel or capillary forms the word "PREGNANT". Typically the word "NOT" is formed in the test flow path and the word "PREGNANT" is formed in the reference flow path. If a sample is applied the device which does not contain any hCG (i.e. the subject is not pregnant), liquid is free to flow along both the test and reference flow paths. A coloured label e.g. a dye, is transported along both flow paths, making the words "NOT" and "PREGNANT" appear as a message in a display. If a sample comprising hCG is applied to the device, agglutination reagents (agglutination ? not gas ?) (e.g. particles of latex coated with anti-hCG antibodies) present in the test flow path reduce the rate of flow so much that liquid in the reference flow path reaches the junction before the liquid in the test flow path can reach the indicator region. This effectively blocks the test flow path, so that the word "NOT" does not become visible and instead the display gives the message "PREGNANT".

The flow path or paths in the assay device may be essentially linear. Alternatively in order to provide a compact configuration, the flow path may follow a serpentine or other convoluted path. The flow path may comprise a bubble retaining means, such as a neck or one or more narrowed portions, which facilitate trapping of the gas bubbles and thus assist in the formation of a block in the flow path to reduce or stop flow. The flow path may comprise a gas bubble trapping or retaining means. For example, the flow path may comprise a channel with two or more overlapping fingers or projections within the base thereof. Such an embodiment may conveniently be formed by a 'serrated' portion, in which a plurality of interdigitated fingers project from opposite sides of the channel into the flow path, which arrangement has been shown to be highly effective in trapping gas bubbles. The flow path may comprise one or projections or elements which serve to enhance the formation of gas bubbles. The projections for example may be jagged teeth like elements. The flow path may comprise nucleation sites, either chemical or physical which serve to enhance the generation of gas bubbles. Other ways in which to enhance the slowing or cessation of flow due to bubbles are to provide one or more flow restriction elements in order to narrow the flow path in its width or height, a hydrophobic region, and an etched surface to increase the surface area of the flow channel. The surface may be etched for example in a grid pattern or comprise a series of parallel etched lines.

Porous structures may be used to slow flow. For example the flow path may comprise a microfluidic channel and a chamber comprising a porous material such as glass fibre or another porous inert material.

In the region where gas bubbles are produced, the flow path may advantageously be substantially sealed to the immediate environment so as to prevent the bubbles from escaping from the fluid sample into the surrounding environment. Thus bubbles may be retained within the device for at least the duration of the test such that they are able to alter the flow rate of the liquid or portion thereof. The flow path (or one or more sections thereof) may be for example a microfluidic channel surrounded by walls comprised of a material that is substantially gas impermeable. Typically the device is completely sealed to the immediate environment apart from the liquid sample application zone or zones and any air vents that may be present within the device.

The assay device may comprise further reagents such as sugars and or proteins such as bovine serum albumin (BSA) which serve to stabilise or influence the resuspension or solubilisation of the one or more reagents present in the assay device.

In another aspect, the invention provides a method of performing an assay, the method comprising the step of applying a liquid sample to an assay device in accordance with aspects of the invention.

In yet another aspect, the invention provides a method of making an assay device, the method comprising the step of depositing in or on an assay device at least one reagent which, during performance of the assay, participates in or catalyses a gas-producing reaction.

According to an embodiment, the assay device may comprise immobilised inhibitor provided immediately upstream and/or downstream of the accumulation zone to inhibit the reaction between any unbound first reagent and second reagent. As such, gas is only generated as a consequence of second reagent reacting with first reagent at the accumulation zone.

A suitable inhibitor is azide which inhibits the reaction between catalase and peroxide to form oxygen gas. For example in a sandwich assay when using liquid samples with no analyte present, much of the labelled reagent does not get bound at the accumulation zone and thus travels downstream of the accumulation zone. The on-coming substrate (peroxide in the case of catalase) reacts with the labelled reagent present downstream of the accumulation zone and generates bubbles. Bubbles formed in this manner are counterproductive as they reduce or stop flow in the test channel when analyte is not present within the sample. The inclusion of an inhibitor of the enzyme downstream of the accumulation zone reduces the formation of bubbles downstream of the accumulation zone. The same effect could be achieved by changing the pH in the channel downstream of the accumulation site to very acid or alkali such that the enzyme activity is abolished or is significantly reduced.

The assay device may further comprise a control assay which is able to indicate that the assay has been carried out correctly. A control assay is useful in determining whether for example the assay device itself has functioned correctly or whether the user has used the device in the correct manner. A number of factors may contribute, either alone or in combination to a device giving a wrong result. There may be for example a defect in one or more of the flow paths, for example a blockage, a deterioration or absence of one or more reagents provided in the test device and so on. The purpose of a control assay is thus to indicate that the test result is valid.

The control assay may be analogous to the test and reference flow paths and may comprise for example a control test flow path and/or a control reference flow path wherein flow in the control reference flow path may be compared to flow in the control test flow path. The control test flow path may for example comprise one or more reagents that generate a predetermined amount of gas to provide one or more bubbles, independent of the amount of analyte present in the fluid sample. The one or more gas generating reagents may the same as employed in the test flow path. The control reference flow path will typically not comprise any gas generating reagents. The test control and reference flow paths may intersect at a downstream junction region. The control assay may comprise one or more indicator regions provided upstream or downstream of the junction zone.

In an embodiment, indicator regions are provided respectively upstream of the junction region in both the control test and control reference flow paths. In use, flow in the control test flow path will be slowed or stopped allowing the flow in the control reference channel to reach the junction first thus choking flow in the control test channel. In so doing the indicator in the control reference channel will indicate to the user that the test has functioned correctly. Conversely if the flow in the control test channel is not slowed or stopped due to the device malfunctioning and not generating bubbles in the control test channel, the flow in the control reference channel reaches the junction first and thus indicates a device malfunction by virtue of an indicator present in the control reference channel upstream of the junction. A common sample application region may connect the test and reference flow paths as well as the control test and control reference flow paths where present.

The assay device may comprise a fluid sample reservoir to which sample may be applied. Thus liquid sample applied to the device may be continuously supplied to the one or more flow paths.

For the avoidance of doubt, it is hereby expressly stated that any feature of the invention described herein as "typical", "preferred", "convenient", "desirable", "advantageous" or the like may be present in the invention in isolation, or in any combination with any one or more other features so described, unless the context dictates otherwise. Equally, unless the context clearly dictates otherwise, features described in relation to one aspect of the invention will generally be applicable in relation to other aspects of the invention.

The invention will now be further described by way of illustrative examples and with reference to the accompanying drawings, in which:

FIGS. 8-11 are schematic representations of other possible embodiments of the invention;

FIG. 12 is a graph of average stopping distance ("No. of loops") against relative amount of conjugate;

The following describes the Figures in greater detail.

Figure 1:
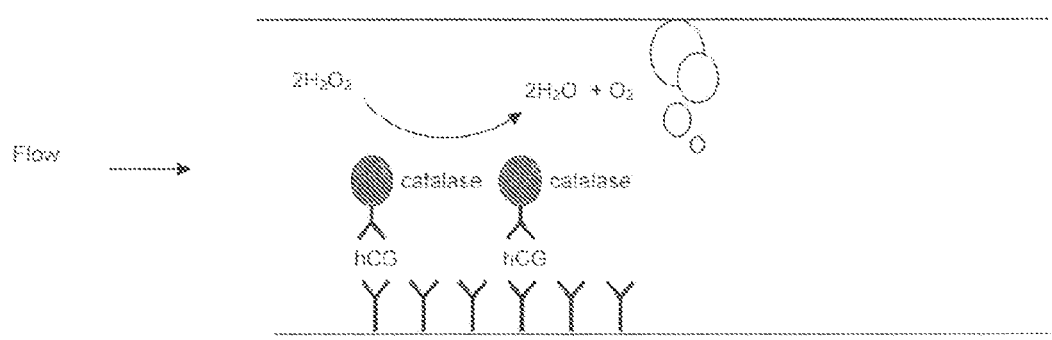
FIG. 1 shows schematically the generation of gas-bubbles by the contact of peroxide with immobilised catalase.

FIG. 1 shows a portion of a device during use for the detection of hCG. An hCG—binding reagent complex labelled catalase is immobilised at the accumulation zone prior to contact with hydrogen peroxide reagent. Upon contact by the hydrogen peroxide, then catalase catalyses the formation of oxygen gas.

Figure 2:
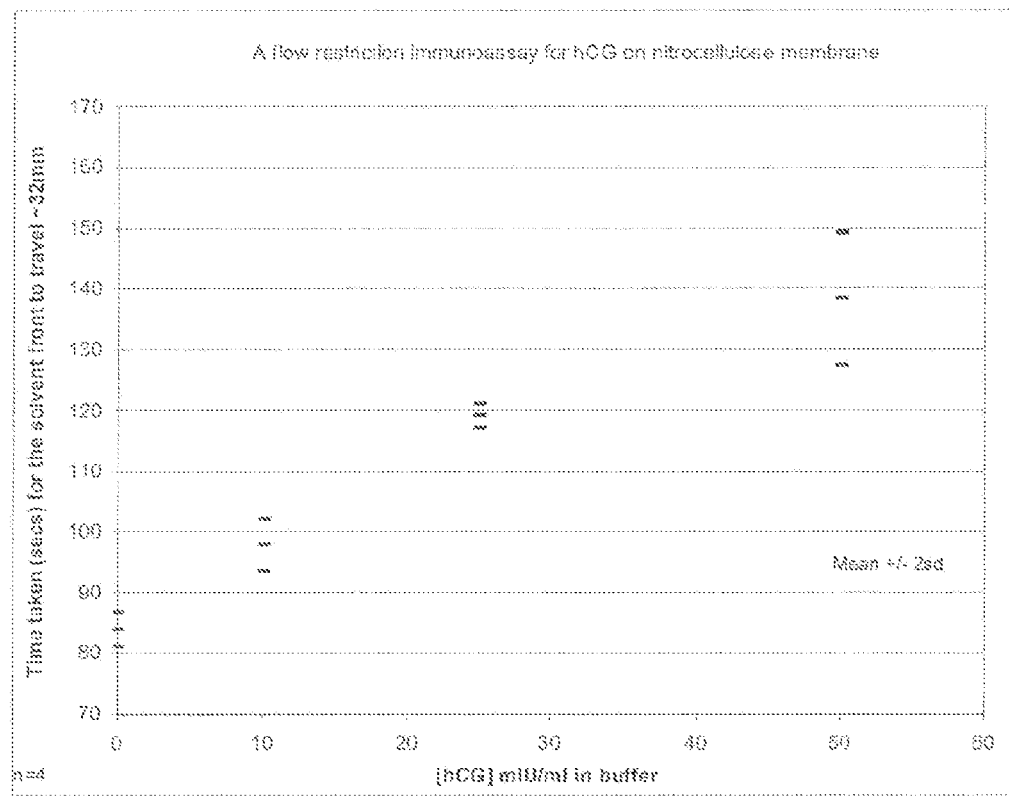
FIG. 2 shows a graph of flow rate vs. analyte concentration for an assay device prepared according to Example 1 below.

FIG. 2 shows a graph of flow rate vs. analyte concentration for various assay devices prepared according to Example 1. A marked change in flow rate of liquid sample along the assay device was seen as the amount of hCG in the liquid sample was varied.

Figure 3:
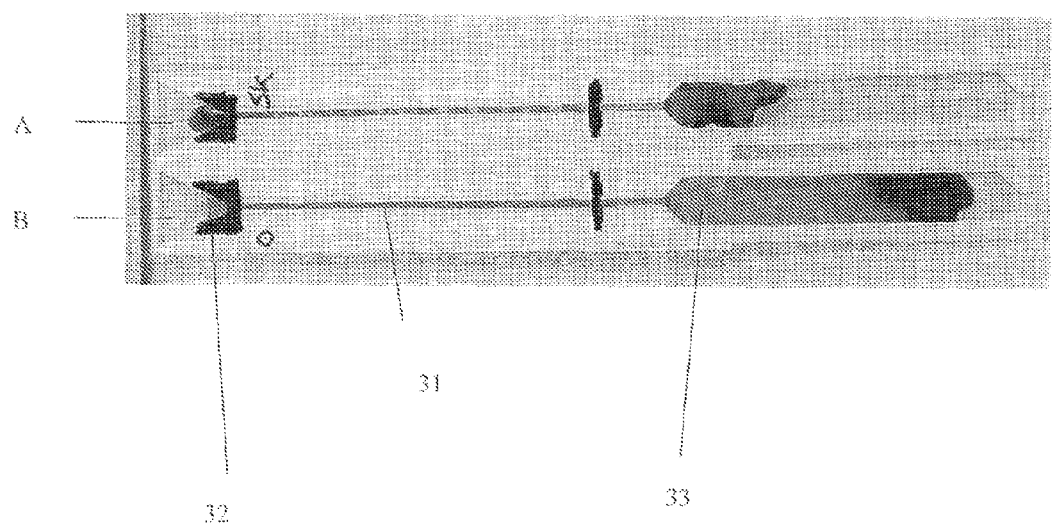
FIG. 3 shows a device prepared according to that of Example 2 below.
Figure 4:
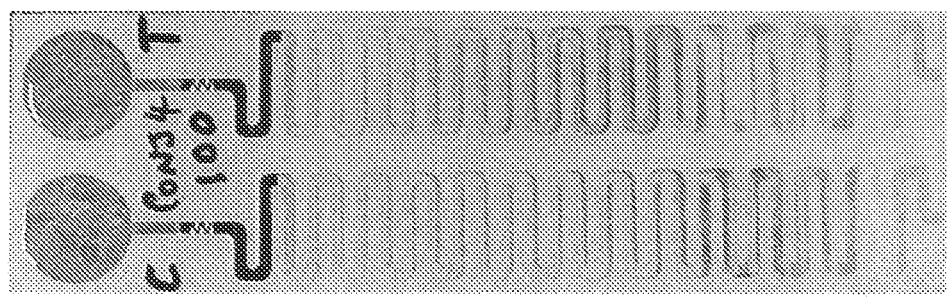
FIG. 4 shows a reference and test channel both having a serpentine path prepared according to Example 3.

FIG. 3 shows a device prepared according to Example 2 comprising a microfluidic test channel (A) and a reference channel (B). The device comprises for each assay an application port (32), a channel (31) and a sink (33). Catalase labelled binding reagent is provided along the length of the channel of the test assay. An aqueous solution of hydrogen peroxide and a visible dye was added to the device whereupon the hydrogen peroxide reacted with the labelled binding reagent in the test—channel to generate gas bubbles. This resulted in a decrease in the flow of the liquid sample along the flow path. The reference channel did not comprise any labelled catalase and no decrease in flow of liquid sample along the reference channel was observed. Hence the dye has nearly completely filled the sink 33 in the reference channel, whilst the dye had filled only a small portion of the sink in the test channel.

Figure 5:
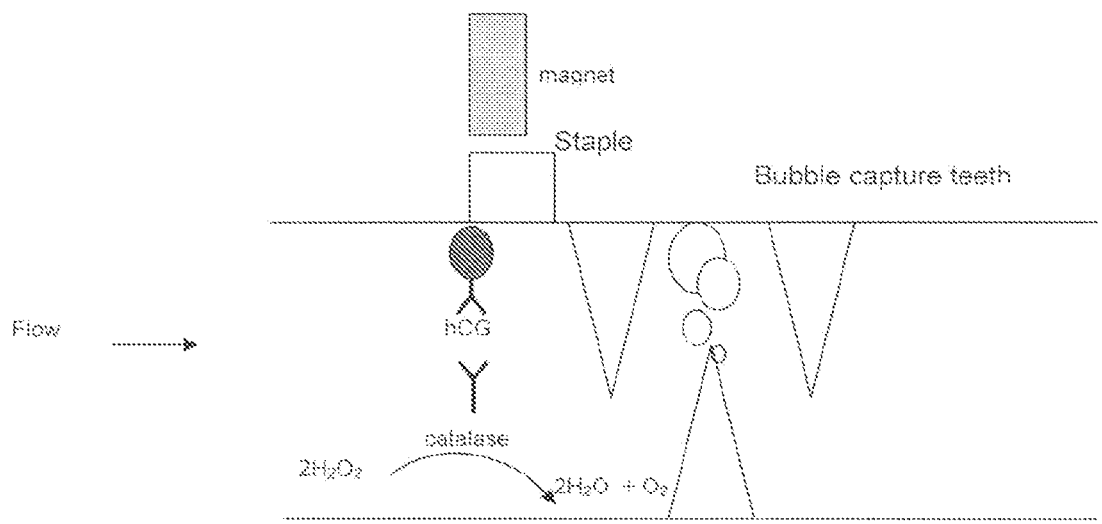
FIG. 5 shows schematically a portion of an assay device prepared according to Example 3.

FIG. 5 shows a portion of an assay device according to an embodiment comprising gas—bubble trapping projections.

Figure 7:
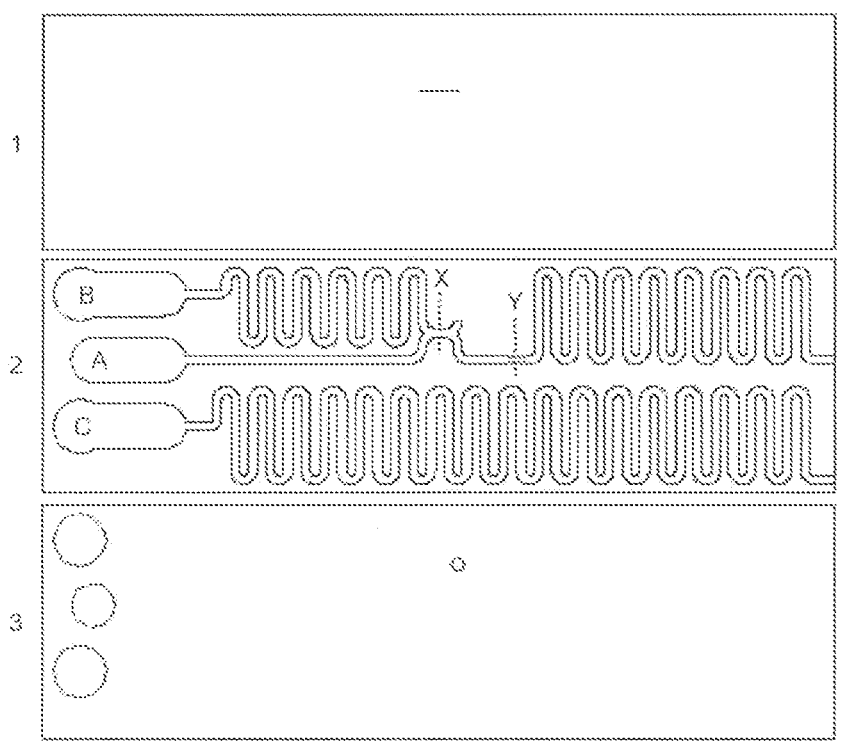
FIG. 7 shows a further assay device according to an embodiment of the invention.

FIG. 7 shows an embodiment of an assay device in accordance with the invention comprising a micro-fluidic gate X (kiss gate) that enables two streams of fluid to be brought together from channels A and B without introducing an air lock.

Figure 8:
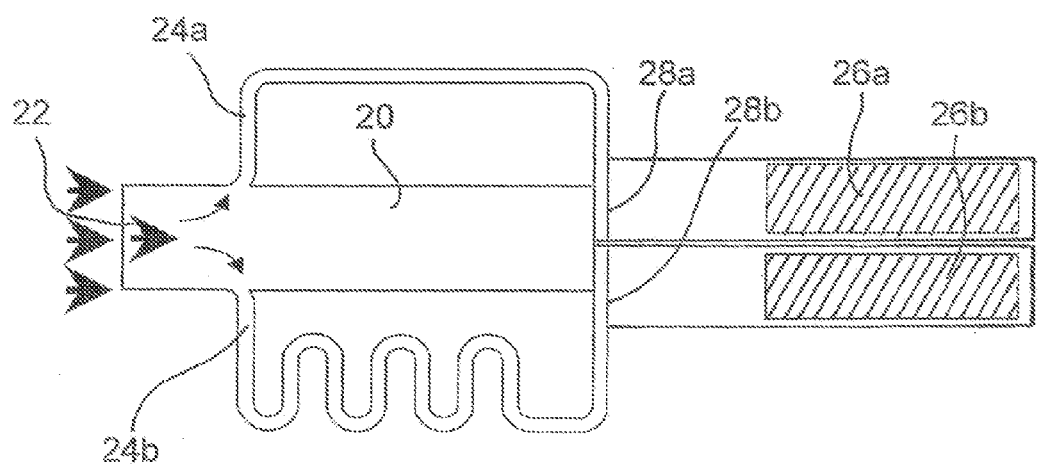
Figure 9:
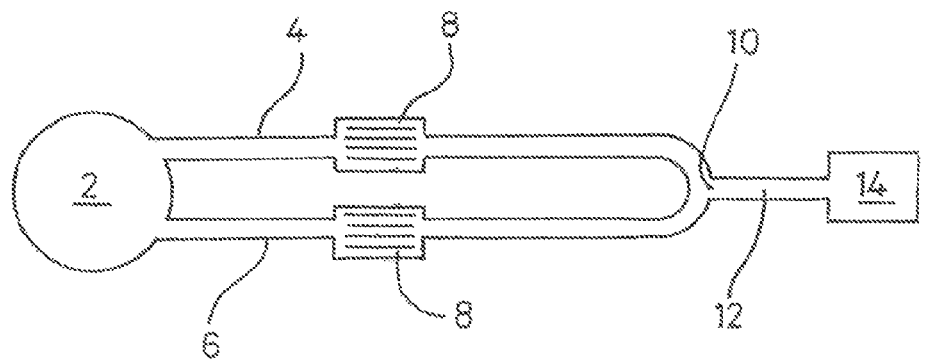
Figure 10:
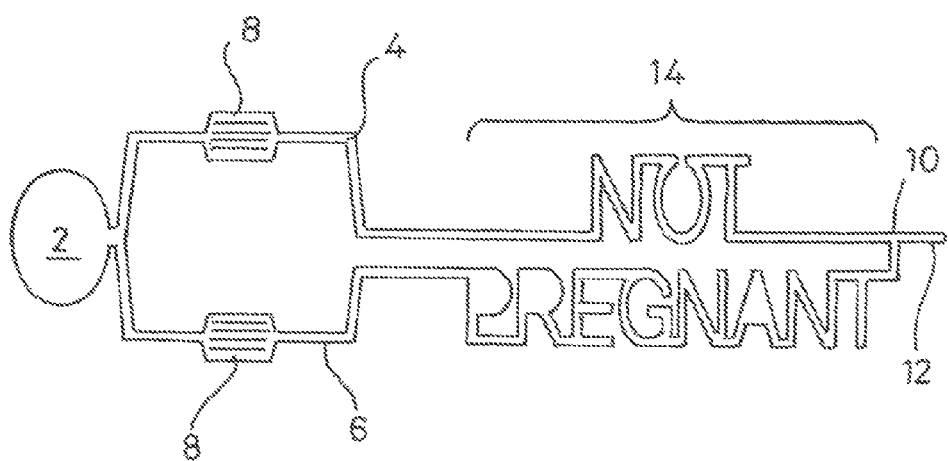

FIGS. 8-10 are schematic representations of various embodiments of assay devices in accordance with the invention. In FIG. 8, there is depicted an assay device capable of giving rise to a digital or binary assay result (a 'yes' or 'no' answer), without the use of any electronics and without an electrical or other power supply. The device comprises a chamber or reservoir 20 having a defined volume. The chamber 20 has an inlet 22 through which a liquid test sample to be analysed can be introduced. Two test flow paths 24a and 24b branch off from the chamber 20 at points equidistant from the inlet 22, such that liquid introduced into the chamber 20 will subsequently start to enter the two test flow paths 24a,b simultaneously.

Two indicator liquid flow paths are provided in the device: one from chamber 20 to downstream indicator region 26a; and one from chamber 20 to indicator region 26b. However, the liquid in the chamber 20 is prevented from advancing by capillarity into either of the downstream indicator regions 26a,b by respective obstacles 28a,b. In this example, the obstacle is created by a break formed by the bore of the respective test flow paths 24a,b, which form T-junctions with the respective indicator liquid flow paths.

In the illustrated example, the same liquid sample acts as both test liquid (flowing along the test capillaries 24a,b) and as indicator liquid (flowing, eventually, from the chamber 20 to one of the indicator regions 26a or 26b). The liquid sample may be, for instance, blood, urine or other body fluid. Within one of the test flow paths 24a,b may be deposited gas-generating reagents which, for example, generate a gas in the presence of the analyte of interest. The gas forms a bubble which blocks the further advance of liquid along the flow path. This is represented in FIG. 8 by flow path 24b being serpentine.

The sample liquid remaining in the chamber 20 functions as an indicator liquid. It substantially fills the chamber but cannot advance past the obstacles 28a,b provided by the capillary breaks constituted by the bores of the test flow paths 24a,b. As explained above, test liquid reaches the end of test flow path 24a before it reaches the end of test flow path 24b, because of the formation of a gas bubble in flow path 24b. The arrival of the test liquid at the end of the flow path 24a abolishes the break, thereby effectively removing obstacle 28a, allowing the indicator liquid to advance from the chamber into the downstream indicator region 26a (which is separate and discrete from indicator region 26b). The entrance of the indicator fluid into the indicator region 26a causes the formation or appearance of a visual signal. This can be achieved in numerous ways, typically by means of a colour change.

The volume of the indicator region 26a is sufficient to accept substantially all of the liquid from the chamber 20.

As the liquid starts to move into the indicator region 26a, liquid in the chamber 20 is drawn away from contact with the obstacle 28b, effectively increasing the size of the break.

Accordingly, if/when test liquid eventually reaches the end of the test flow path 24b, it will have no effect and the indicator liquid in the chamber 20 will still be unable to enter the downstream indicator region 26b.

FIGS. 9 and 10 schematically illustrate variants of this concept, which again provide a "Race" assay giving a digital or binary assay result readout.

The device shown in FIG. 9 has a sample application region 2 fluidically connected to test flow path 4 and a reference flow path 6, which both comprise a capillary channel. A filter 8 may optionally be provided in one or both of the flow paths. The flow paths converge downstream at a junction region 10 leading to a common channel 12. An indicator region 14 may be provided downstream from the junction region 10.

Liquid sample applied to the device via a sample application port in the sample application region 2 is able to flow respectively along the test and reference flow paths 4, 6 and towards the junction region 10. One or more vents are provided in the common channel 12 and the indicator region 14 to allow air to be displaced from the device by the advance of liquid along the capillaries. However, once one of the fluid fronts has reached the junction region 10, it blocks off the other flow path from the vents, preventing further advance of the liquid along the other flow path. Thus the device only allows for the arrival in the indicator region 14 of fluid flowing along the flow path whose fluid front first reaches the junction region 10. An indicator region may be provided in the fluid channels to enable an observer to determine which fluid in the respective channel arrived first. For example dyes of different colours may be provided in each channel such that the fluid sample is able to interact with the dye to produce liquid of a particular colour. Thus the presence of a particular coloured dye in the indicator region would enable a user to determine which fluid reached the fluid gate first.

The relative rate of advance of liquid along the flow paths 4, 6 may be affected by causing the formation of a gas bubble in an analyte—specific manner in one of the flow paths e.g. by providing gas-generating means immobilised in the flow path which generates a gas in response to the presence of the analyte of interest.

Another embodiment is illustrated in FIG. 10.

As in the previous embodiment, the assay device comprises a sample application port in a common sample application region 2, from which liquid sample can flow into a capillary forming part of the test flow path 4 and a separate capillary forming part of the reference flow path 6. Alternatively each flow path may be provided with a unique, separate sample application region. Those skilled in the art will appreciate that the assay device described in the present examples may be provided with further test flow paths to test for the presence of further analytes of interest. The or each further test flow path can, if desired, be provided with a corresponding reference flow path.

In the embodiment depicted in FIG. 2, each flow path comprises a filter element 8 and an indicator region 14, upstream of a junction region 10.

The filer element 8 comprises one or more gas-generating reagents. In the presence of the analyte of interest (in this instance, hCG) reagents generate a gas which forms a bubble, blocking the flow path 4.

Each flow path is also provided with a coloured dye which is mobilised by contact, and migrates, with the liquid sample.

The indicator region 14 of each flow path comprises a capillary channel forming the word "NOT" in the test flow path 4 and the word "PREGNANT" in the reference flow path. These capillaries are formed from clear synthetic plastics material and are against a low contrast background (e.g. white or clear synthetic plastics material). Accordingly, prior to performance of the assay, the capillaries are not highly visible.

However, once the assay is initiated, the dye located in the flow paths upstream of the indicator region is mobilised by the advancing liquid sample. If the sample does not contain hCG, liquid is free to flow along both flow paths. The dye-containing liquid thus fills both capillaries, displaying the assay result "NOT PREGNANT". Vents may be provided at several points along the reference flow path to encourage the flow of liquid therealong. In particular these vents may be provided to assist the liquid in filling the indicator region of the reference flow path. Preferably there are no such vents in the test flow path, air being vented from the test flow path capillary 4 only via one or more vents downstream of the junction region 10, in the common channel 12, such that if liquid flowing along the reference flow path 6 reaches the junction region 10 before the liquid front flowing along the test flow path 4, air can no longer be displaced from the test flow path capillary and further advance of the liquid along that channel is prevented.

The rate of flow of liquid along the test and reference flow paths, and/or the length of the respective flow paths, is adjusted such that, in the absence of hCG, liquid flows along both flow paths 4, 6 and fills the respective indicator regions. Typically, in the absence of hCG in the sample, the liquid flowing along the reference flow path will reach the junction region 10 either simultaneously with the liquid flowing along the test flow path or just 1 or 2 seconds in advance thereof.

If however the applied sample comprises hCG, gas generation and bubble formation will take place in the test flow path 4 which substantially retards the advance of liquid along the test flow path capillary towards the indicator region. This allows liquid flowing along the reference flow path to "win the race" to the junction region easily. The liquid flowing along the reference flow path reaches the junction region 10 before the liquid flowing along the test flow path 4 reaches the indicator region. In this instance, the word "NOT" does not become filled with dye and remains indistinct, whilst the word "PREGNANT" becomes highly visible and thus displays the assay result.

Figure 13:
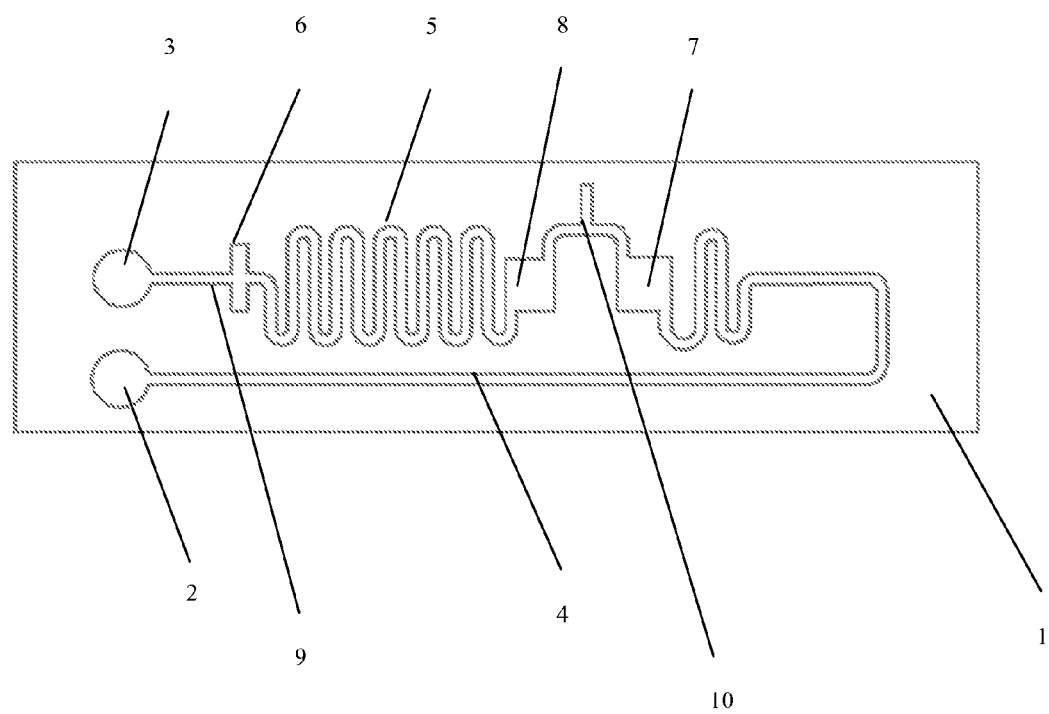
FIG. 13 shows a further device in accordance with an embodiment of the present invention.

FIG. 13 shows device 1 comprising a reference flow path 4 and a test flow path 5 with sample application regions 2 and 3 connecting respectively the reference and test flow paths. Also shown is a bubble trapping region 6 and test and reference indicator regions 8 and 7. A junction region is indicated at 10 and an accumulation zone shown at 9. An assay carried out using the device of FIG. 13 is described in Example 5. The reference channel as shown in the figure is mostly linear with a serpentine shape at its distal end whereas the test channel is mostly serpentine in shape. The convoluted shape of both channels was employed in this case in order to make the device more compact.

Figure 14:
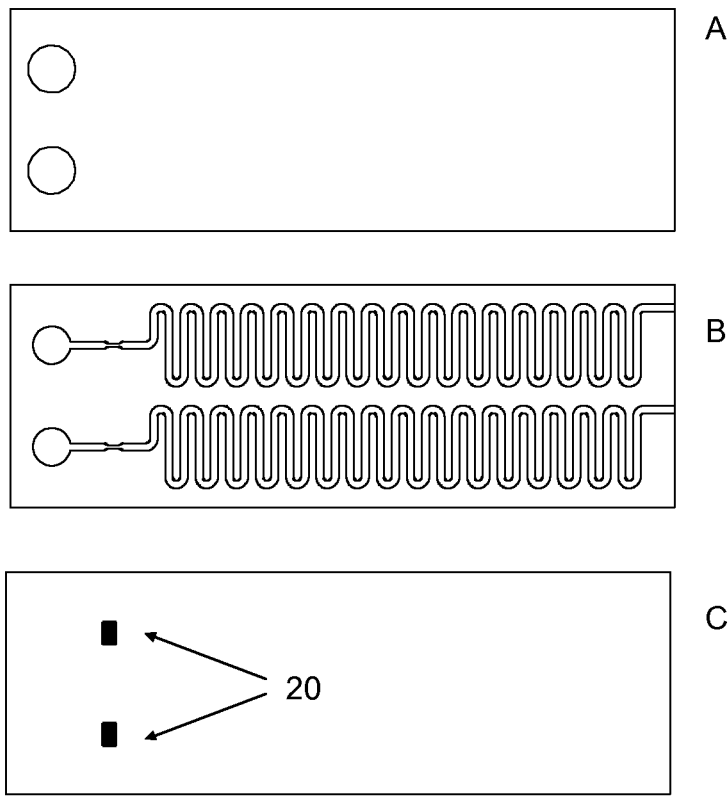
FIGS. 14 and 15 show respectively sublayers of a device and the completed device in accordance with an embodiment of the present invention.
Figure 15:
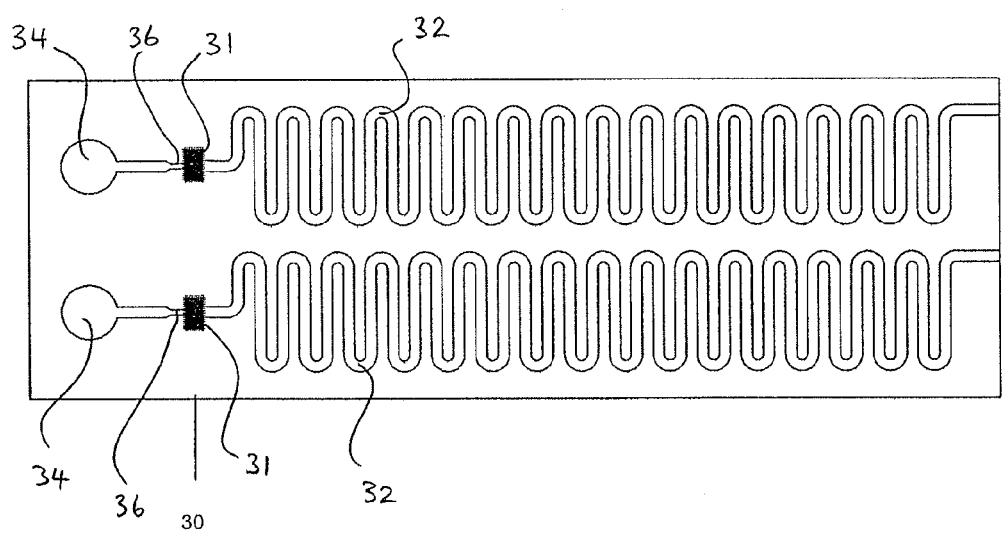

FIGS. 14 and 15 shows respectively the sublaminates of a device A, B and C and the completed device 30. Device 30 comprises two test channels 32 of identical shape and dimensions each comprising an etched bubble trap 31 and sample application zones 34.

Example 1

A Flow Restriction Immunoassay for hCG Comprising a Nitrocellulose Porous Carrier An assay device was prepared as follows:
Preparation of Reagents:
The co-immobilisation of anti-αhCG and catalase onto blue polystyrene latex particles.
Materials
Duke Scientific blue polystyrene latex particles 400 nm diameter 10% solids (w/v) lot CB1860
BDH Analar 95% Ethanol plus 0.5% sodium acetate (Sigma)
Intergen Bovine Serum Albumin (BSA) Cohn 5YT 19202 prepared as 200 mg/ml in deionised water
Anti-α hCG internal clone 3299 lot PL 1257 3.4 mg/ml in PBSA
Sigma catalase from human erythrocytes 90% pure SDS-PAGE C3556 lot 116K1463 at 52200 units/mg protein supplied in 50 mM Tris pH 8.0
10 mM borate buffer pH 8.5
Method
1. Dilute latex particles to 0.5% solids (w/v) in 10 mM borate buffer (prepare 1 ml of diluted latex in a 1.7 ml Eppendorf tube).
2. Centrifuge the Eppendorf tube at 17,500 rpm (25,848 rcf) @ 15° C. on an Heraeus Biofuge 17RS centrifuge for 5 minutes.
3. Remove the supernatant and re-suspend the pellet into 1 ml 10 mM borate buffer.
4. Place 100 µg of catalase into a fresh 1.7 ml Eppendorf tube and add 100 µg of anti-hCG.
5. Add the washed latex from step 3 into the Eppendorf tube of step 4 and mix well by repeated filling and emptying of the micro-pipette (~6 filling and emptying cycles).

6. Immediately add 200 µls ethanol-acetate and mix well on a mixer for ~5 seconds.
7. Place the Eppendorf tube on an end-over-end mixer (~60 rpm) for 60 minutes at ambient temperature.
8. Add 50 µls of 200 mg/ml BSA and continue to mix on an end-over-end mixer (~60 rpm) for 30 minutes.
9. Repeat step 2, remove and discard the supernatant. Re-suspend the pellet into 1 ml of 10 mM borate buffer. Add 50 µls of 200 mg/ml BSA and mix well.
10. Repeat step 2, remove and discard the supernatant. Re-suspend the pellet into 1 ml of 10 mM borate buffer. Add 50 µls of 200 mg/ml BSA and mix well.
11. Repeat step 2, remove and discard the supernatant. Re-suspend the pellet into 1 ml of 10 mM borate buffer. Add 50 µls of 200 mg/ml BSA, mix well and store overnight at 4° C.
12. Repeat step 2, remove and discard the supernatant. Re-suspend the pellet into 1 ml of 10 mM borate buffer. Add 50 µls of 200 mg/ml BSA and mix well.

The Preparation of Nitrocellulose Membrane with an Immobilised Zone of Anti-β hCG Materials 8 µm nitrocellulose membrane on a Mylar support
Monoclonal anti-β hCG internal clone 3468 at 3 mg/ml
Sigma 1% (w/v) polyvinyl alcohol (PVA) 10,000 mwt plus 3% (w/v) sucrose
(Sigma 58501) in deionised water (blocking buffer)

Method

1. Deposit the anti-β hCG at 3 mg/ml using a metered pump and syringe to produce a zone on the nitrocellulose membrane ~1 mm wide and ~300 mm in length (deposited at ~0.1 µls/mm).
2. Dry the nitrocellulose membrane at 50° C. under warm air for ~10 minutes. Apply the blocking buffer to one end of the membrane and allow it to wet the membrane running parallel to the length of the test line until it saturates the membrane.
3. Dry the nitrocellulose membrane at 75° C. under warm air for ~10 minutes.
4. Cut the membrane into strips ~6 mm wide and 40 mm in length having a test zone of anti-β hCG running across its width (6 mm), the test line being ~10 mm from the base of the strip.

Protocol for Conducting a Flow Restriction Immunoassay for hCG

1. Arrange strips of nitrocellulose membrane on a vertical support with the proximal end of the test strip touching the base of the lab bench (test line positioned ~10 mm for the base). Apply gel blotting paper as a sink to the distal end of the test strips.
2. Prepare a mixture of 10 µls latex coated in anti-α hCG plus 50 µls buffered standard (PBSA) containing 0 mIU/ml hCG. Apply this mixture to the base of the test strip and allow it to chromatograph through until dry at the base. Apply 50 µls of borate buffer to the base of the strip and allow it to chromatograph through until dry at the base.
3. Dry the test strips at ambient temperature for ~3 hours.
4. Apply an adhesive laminate film (ARCare 7759 co #D9012) to the surface of the nitrocellulose membrane, running ~2 mm from the proximal end of the membrane to the distal end such that it covers the entire width of the strip.
5. Sandwich the test strip between two microscope slides and hold these together with crocodile clips. Stand the test strip vertically with the proximal end in contact with the lab bench.
6. Apply 50 µls of 5% $H_2O_2$ (v/v) (diluted from a stock of 30% $H_2O_2$ Sigma H-1009 lot 021K3250 using deionised water plus 5 mg/ml BSA) to the base of the test strip and allow to chromatograph. Observe the movement of the solvent front and record the time taken for the solvent front to travel a distance of 32 mm from instance of applying the $H_2O_2$.
7. Repeat the above to generate 3 further replicates of test strips run with 0 mIU/ml hCG.
8. Repeat the above to generate 4 test strips each run with 10, 25 and 50 mIU/ml hCG buffered standards.

A graph was plotted for the amount of hCG analyte present in the sample vs. time taken for the liquid sample solvent front to travel along the porous matrix.

The graph is illustrated in FIG. 2. From FIG. 2 it can be seen that the presence of hCG analyte in the liquid sample results in a decrease of the flow rate of the liquid sample.

Example 2

Capillary Assay Using Oxygen Bubbles to Stop Flow in an Analyte-Dependant Fashion Capillary Construction:
Base: Polystyrene microscope slide
Middle: ~10 µm double sided white PSA tape (Adhesive Research ARCare 7840)
Top: 175 µm polyester film (antistatic treated)
2×1 mm capillaries were made in the white PSA tape along the length of the microscope slide. (see below)
Volume Collection Chamber:
Base and top: 175 µm polyester film (antistatic treated)
Middle: ~10 um double sided white PSA tape (Adhesive Research ARCare 7840)
6 mm chamber tapering to 1 mm at each end, that can be stuck onto the capillary slide for the last step of the protocol. (see below)

Assay Format:
Protocol for Both Channels

1. Apply 15 µl of 3468 at 2.03 mg/ml Batch PL1322 along the length of the channel and leave for ten minutes.
2. Apply 20 µl of 5 mg/ml beta casein in PBS. Leave for ten minutes.
3. Apply further 5 mg/ml beta casein, 10×5 µl channel.
4. Load with 5×5 µl of 5K mIU/ml hCG std or 0 std made in 5 mg/ml beta casein. Leave five minutes.
5. As for 3.
6. Load 5×5 µl of 0.05% (BR101007) 3299-catalase latex particles (400 nm). Leave 20 minutes.
7. Wash 20×5 µl PBS, then 2×5 µl red dye/channel.
8. Attach collection chamber and start video.
9. Add 5 µl of 1% hydrogen peroxide in PBS with ⅙ blue dye. Leave for 10 minutes then follow with further 5 µl lots of hydrogen peroxide.

Example 3

Capillary Assay Using Oxygen Bubbles to Stop Flow in an Analyte-Dependant Fashion A micro fluidic type capillary assay was constructed wherein the first binding reagent—analyte-labelled binding reagent complex was immobilised or captured at a reaction zone by means of a magnet. According to this example, the first binding reagent was labelled with a magnetic particle.

Capillary Construction:

Base and top: 175 μm polyester film (antistatic treated) HiFi PMX 715

Middle: ~10 um double sided white PSA tape (Adhesive Research ARCare 7840)

2×1 mm capillaries were made in the white PSA tape along the length of the device in an snake pattern. At the sample application end a large circle was cut out and in the straight channel before the pattern are a series of "sharks" teeth. Underneath the device just in front of the teeth a staple and a magnet were arranged in a fashion to focus the magnetic field to allow capture of 1 μm magnetic beads.

Protocol

1. Prepare test and control samples:
   Reagents: hCG stds, azide free. In 1 mg/ml BSA+0.05% ProClin 300 3468 magnetic beads (Dynabeads—MyOne tosylactivated) 3299-Catalase conjugate (glutaraldehyde DT C1 29/11/07)
   Control: 5 μl of magnetic beads, 5 μl C1 conjugate and 10 μl 1hCG
   Test: 5 μl of magnetic beads, 5 μl C1 conjugate and 10 μl 500 mIU/mlhCG
2. Add 2 μl of dye solution. (¼ blue food dye)
3. Add 2 μl of particle/conjugate/hCG mix to T or C channel
4. Add 60 μl of 1% hydrogen peroxide to each channel
5. Monitor dye front along capillaries (video)

Figure 6:
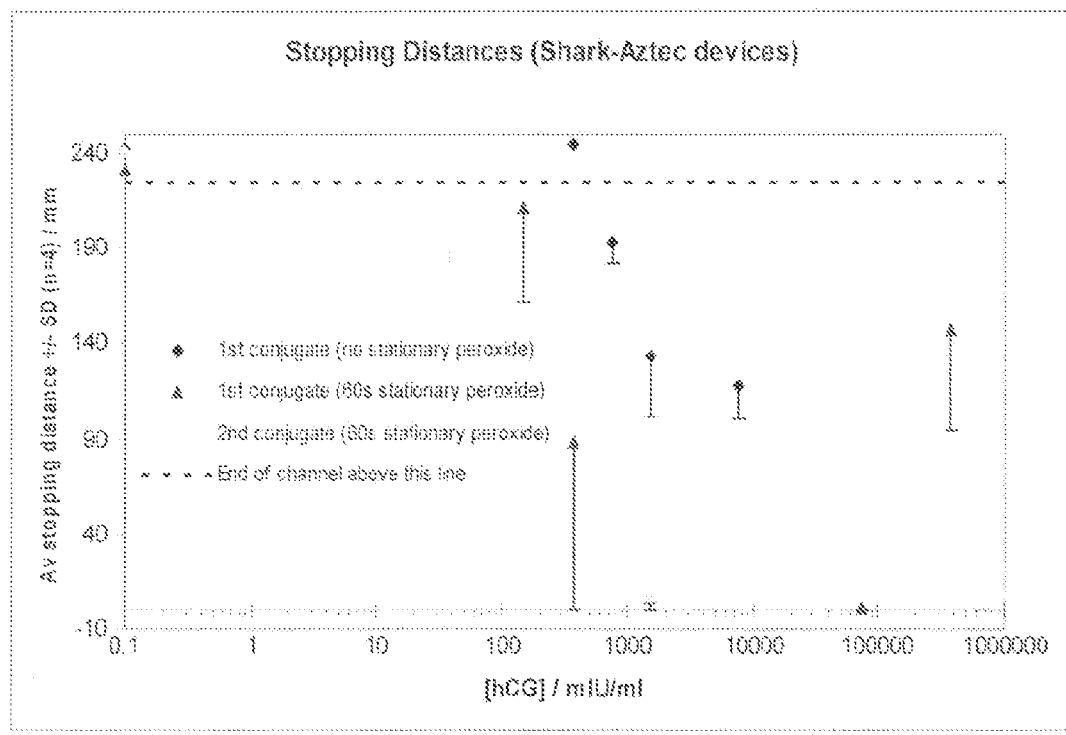
FIG. 6 shows a graph of flow rate vs analyte concentration for assay devices prepared according to Example 3.

A number of such devices were prepared and tested with a number of liquid sample comprising varying concentrations of hCG analyte and the distance in mm that the liquid fluid front flowed along the channel (stopping distance) was measured. The graph of stopping distance vs hCG concentration is shown in FIG. 6.

The assay device shown in FIG. 7 can be used to allow a first fluid in reservoir A and a second fluid in reservoir B to flow along their respective channels and meet at a junction or gate (x). Furthermore the construction is such that liquid from a first reservoir (A) flows along the flow-path to reach an immobilisation zone (Y) prior to the arrival of liquid at the immobilisation zone from the second reservoir (B). Reservoir B (or the flow-path downstream from it) may contain the second reagent and reservoir A (or the flow-path downstream from it) may contain the labelled first reagent. A reference channel C is also provided.

FIG. 7 shows schematically the three layers used to construct a micro fluidic gate (kiss gate) that enables two streams of fluid to be bought together without introducing an air lock.

Base and top (71&73): 175 μm polyester film (antistatic treated) HiFi PMX 715

Middle (72): ~100 μm double sided white PSA tape (Adhesive Research ARCare 7840)

The base layer (71) has a groove scored in it on the hydrophilic side of the polyester film at the position where the two streams of fluid meet. The middle layer (72) is used to construct channels that are ~1 mm wide comprising the test channel with two feeds A & B and a reference channel C. The top layer (73) is adhered hydrophobic surface side down onto the PSA middle layer and has holes cut in it to allow sample to be applied simultaneously to fluid channels A, B and C. Top layer 73 also has an aperture which acts as a vent at the end of channel A.

Immunoassay reagents are dried in reservoir A and hydrogen peroxide generating reagents (for example urea hydrogen peroxide) are dried in reservoir B.

When sample is applied simultaneously to all three reservoirs, flow occurs in the three flow-paths.

Immunoassay reagents (e.g. antibody coated magnetic beads and catalase-antibody conjugate in an assay for example for hCG) are rehydrated by the sample and pass down channel A. On reaching the intersection with channel B the score line in the hydrophilic base prevents liquid crossing into channel B and so flow continues down to the end of the channel. In the presence of analyte the immune complex formed is captured at the serrated part of the channel (test or capture zone Y), downstream of the kiss gate.

Hydrogen peroxide generating reagents are rehydrated in chamber B and pass down the longer channel B to the intersection with channel A (kiss gate). When fluid in channel B reached the kiss gate the presence of fluid in channel A allows the now generated hydrogen peroxide to cross over into channel A. Sample volumes delivered to reservoirs A and B are such that reservoir A becomes exhausted by the time fluid in channel B reaches the kiss gate, this so that flow switches from 100% A flow to 100% B flow. When hydrogen peroxide passes over the immune complex at Y, oxygen is generated forming a bubble with slows or stops flow.

Structures may be introduced into the reservoirs to aid uniform drying and slow release of the reagents upon rehydration. The shape, height, surface properties and density of these structures influence the drying and rehydration process. Addition of a pillar (full height, ~1 mm diameter circle of 100 μm PSA tape) into the reservoir just in front of the entrance to the channel can be used to funnel the rehydrated complex down the centre of the channel and not down the sides where flow is influenced by the walls of the channel. This allows more complete and faster evacuation of the reagents from the reservoir.

Example 4

Dried Conjugate Reagent.

This consisted of a 1 micron diameter magnetic latex with adsorbed anti-beta hCG (clone 3468)—3468 magnetic beads, a conjugate made of human erythrocyte catalase linked to anti-alpha hCG (clone 3299), and further comprising BSA, sucrose, phosphate buffered saline, pH 7.4 containing 0.05% ProClin 300 were mixed in accord with table 1.

TABLE 1

| Mixture | 6A | 6B | 6C | 6D |
| --- | --- | --- | --- | --- |
| 3468-mag beads (40 μg 3468) 10 mg/ml/μL | 70.4 | 91.5 | 70.4 | 70.4 |
| 50% w/w sucrose/μL | 21.12 | 27.5 | 21.12 | 21.12 |
| BSA 200 mg/ml in PBS, 0.05% PC300/μl | 14.4 | 18.2 | 14.4 | 14.4 |
| 1 mg/ml BSA in PBS, 0.05% PC300/μl | 12.6 | 14 | 7.2 | 0 |
| Conjugate 11/uL | 1.8 | 4.7 | 7.2 | 14.4 |
| Rel amt conjugate | 1 | 2 | 4 | 8 |
| Dry state: sucrose % w/w | 74.7 | 75.1 | 74.7 | 74.7 |
| Dry state: BSA | 20.4 | 19.9 | 20.4 | 20.4 |
| Dry state: mag beads | 5.0 | 5.0 | 5.0 | 5.0 |

Four microliters of reagent were dried on appropriate areas of the lids of test devices, dried in air then left to dry overnight in a desiccator loaded with a molecular sieve. Devices were assembled and tested by first rehydrating the reagent with 3 μL of hCG solution in PBS, 0.1% ovalbumin, 0.1% sodium azide pH 7.4 for 60 s then chasing this to the magnetic capture zone and then 10 μL of hydrogen peroxide in 1 mg/ml BSA in PBS, 0.05% PC300 was added to the peroxide reagent zone and left in contact with the captured particle bed for 60 s before instigating flow with a second addition of 35 μL of the same peroxide solution to the peroxide reagent zone. The distance moved by the liquid meniscus along a the serpentine channel was measured and the average of several replicate measurements plotted in FIG. 12. FIG. 11 is a schematic view of an assay device similar to that employed in this example.

In FIG. 12 data at 8 loops or more indicated that the meniscus ran to the end of the device (1 loop=20 mm in length). Clearly the mobilised reagent, which forms a bed of magnetic material, can capture catalase in the presence of hCG and stop fluid flow.

Hydrogen Peroxide Reagent.

A solution of 131 mg urea:peroxide powder (made by grinding a tablet of Fluka product 95314, lot 1326053) and 47 mg sucrose dissolved in 0.75 ml PBS, 0.05% ProClin 300, pH 7.4 was set to pH 6.9 with 2M NaOH. Two 4 µL volumes were dried onto the base of the device in region B and dried in a stream of air at room temperature (ca 22° C.), then placed in a desiccator containing a molecular sieve desiccant. The base at region B was scratched to enable it to grab the reagent and localise it when it was pipetted onto it.

To test:
1. Add 8 µL of (50 mL of 10 mg/ml) 1 mm diameter magnetic latex beads with anti-beta hCG bound, 75 mL of 0.0054 mg/ml 1 mm diameter magnetic beads with catalase bound and 75 mL of 1 mg/ml bovine serum albumin in phosphate buffered saline, (0.05% ProClin 300, pH 7.4) to region A to deliver some catalase particles and anti-beta hCG particles to the capture magnetic staple where they form a line at C. Mark the position of the meniscus.
2. Add 7 mL of 1 mg/ml BSA, in PBS, 0.05% ProClin300, pH7.4 (buffer A) to the dried urea:peroxide reagent at region B, leave 60 s to hydrate. The meniscus stops short of the kiss gate.
3. Add 30 mL of buffer A to region B to chase the dissolved urea:peroxide through the magnetic bead bed. Mark the position at which the meniscus stops moving.

Result:

Bubbles were generated in and near the magnetic bead bed which stopped flow, indicating that peroxide was being delivered to the bed. The stopping distances were 1, 1.3, 0.8, 1.3, 1.7, 0.6 loops (1 loop=20 mm length of the serpentine capillary).

Further work indicated that there was some dependence upon the % of sucrose in the dried reagent, the volume of reagent dried and the depth of the texturing on the base. From this initial work the recipe detailed above, with 26% sucrose in the dried formulation, was the best of three tested (the samples contained 0, 26% and 42% sucrose respectively in the dried formulation).

Example 5

A device according to FIG. 13 was prepared as follows:

Two untreated polyester layers of dimensions 25 mm width×90 mm length×175 um height and one of 25 mm width×90 mm length×100 um height were prepared (HiFi PMX 739) to form respectively the base, lid and gasket of the diagnostic device.

The underside surface of the lid was treated with an antistatic hydrophilic coating (HiFi PMX 715) and the microfluidic design as shown in FIG. 13 was cut out of the gasket using a Graphtec plotter. Glue was applied to the upper and lower surfaces of the gasket and the three layers laminated together. The resulting device had microfluidic channels having a hydrophilic roof and untreated walls and a floor.

The height of the channels was 100 um and the width 1 mm. The length of the reference channel from the sample application zone 2 to the indicator region 7 was approximately 12 mm and the length of the test channel from the sample application zone 3 to the indicator region 8 was approximately 11.5 mm. The bubble trap 6 comprised glass fibre (Millipore G028) of dimensions 1 mm width×5 mm length. The accumulation zone 9 was located 1 mm upstream of the bubble trap. The indicator zones each comprised a 4 mm$^2$ Whatman No. 1 chromatography paper containing Brillinat Blue R colour indicator.

A 2 ul incubated mixture of antibody to hCG (in house clone 3468) attached to a 1 um magnetic particle, hCG (10, 000 mIU/ml), and a second antibody to hCG (in house clone 3299) labelled with catalase was added to the sample application region 3. The magnetic particles was drawn and held at the accumulation zone 9 by means of a magnet. 6 ul of PBS buffer was thereafter added to sample application zone 3 in order to wash the labelled complex. 10 ul of 0.5% peroxide in PBS and 10 ul of PBS were added simultaneously to the sample application regions 3 and 2 respectively. Peroxide reacted with the catalase at the accumulation zone to generate bubbles which were trapped at the bubble trap 6 and which stopped flow in the test channel. Flow continued in the reference channel which was indicated by the change in colour in the indicator region 7. No colour change was observed in the indicator region 8. Flow was arrested in the test channel between 34 and 40 seconds after application of peroxide to the sample application zone 3.

Example 6

A device was prepared in accordance with the device shown in FIGS. 14 and 15. The external dimensions of the device and the height width, length and materials of laminates A, B and C were the same as used in the device according to Example 5.

A 3 mm×2 mm portion of the upper surface of laminate C was etched with a Graphtec plotter in a hashed design comprising a number of etched lines having a separation of 0.2 mm to provide a bubble trap. The resulting bubble trap in the finished device was 1 mm width×2 mm length.

The channel at 36 in FIG. 15 was restricted in its width in a small area upstream of the bubble trap to aid the collection of the bubbles and enhance their restriction in flow.

The assay protocol was as follows:
Magnetic particles from Ademtech (pre-coated in Streptavidin) coated in biotinylated anti-β hCG.
Assay buffer PBS plus 1 mg/ml BSA (bovine serum albumin)
Buffer hCG standards in assay buffer
Airbrushing buffer (100 mM Tris plus 10% BSA and 20% sucrose pH 9)
Anti-α-hCG linked to catalse by glutaraldehyde conjugation C12: diluted 1:4 in assay buffer
Sigma stock peroxide solution 30% (w/v)
1. Prepare the magnetic beads in air brushing buffer @1% solids
2. Mix 5 µls of magnetic beads in air brushing buffer with 5 µls of buffer standard containing 0 hCG. Add 2.5 µls of diluted conjugate C12 and incubate the mixture for 90 seconds at room temperature.
3. Arrange a laminated device with a magnetic trap positioned ~1 mm upstream of the constricted area of the channel.
4. Apply 2 µl of the above mixture to the channel and let this run through. The magnetic beads were seen to collect at the trap area.
5. Apply 6 µls of assay buffer to the device and let this run through. Mark the point reached by the solvent front once flow stops.

6. Add 40 µls of peroxide at 0.5% (v/v) (prepared in assay buffer) to the device and observe the time taken for the flow to stop.
7. Repeat the above using fresh reagents and a new laminated device.
8. Repeat the above using hCG standards containing 20,000 or 2,500 or 312 or 156 mIU/ml hCG such that two replicates were produced for each level of hCG.

Results

The flow in devices ran with 0 hCG was not arrested, the liquid was seen to move to the end of the test channel. The flow in the device run with the levels of hCG tested could be discriminated from the devices ran with 0 hCG (on +/−2 sd).

Figure 16:
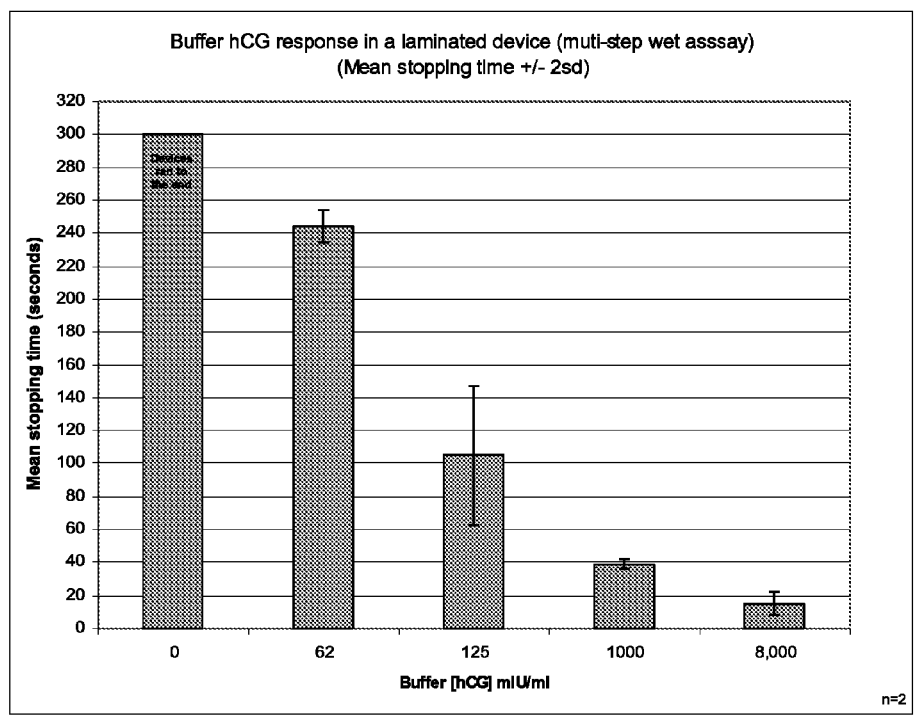
FIG. 16 shows a graph of the mean stopping time for buffer samples containing hCG of various concentrations applied to the device as shown in FIG. 15 and as described in Example 6.

The mean stopping time in sec for a number of buffer samples containing hCG is shown in FIG. 16. The concentrations of hCG reported in the graph are the actual hCG levels produced upon dilution as created in step 2 above. As can be seen from this Figure, increasing the level of hCG resulted in a decrease in the mean stopping time.

The invention claimed is:

1. An assay device for determining the presence and/or amount of an analyte of interest in a liquid sample applied, or otherwise introduced, to the device, the device comprising:
   at least one assay flow path along which a liquid flows;
   an accumulation zone comprising means for retaining a labelled reagent in an analyte-dependent manner;
   a gas generating means which generates a gas dependent upon the presence, absence or amount of analyte, the gas-generating means including the labelled reagent;
   wherein the gas creates one or more bubbles in the liquid sample which acts to alter the flow of liquid along the flow path to a downstream zone; a bubble-retaining means upstream from said downstream zone which facilitates the trapping of gas bubbles in the flow path to reduce or stop flow of liquid therealong; and
   a detection means to detect any alteration in flow of liquid and/or an indicator means to detect the presence or arrival of liquid at the downstream zone; wherein an assay result is determined by detecting the alteration of flow of liquid along the flow path and/or by detecting the presence or arrival of liquid at the downstream zone.

2. The assay device according to claim 1 wherein the gas generating means comprises first and second reagents, and one of the reagents is the labelled reagent.

3. The assay device according to claim 2 wherein one of the reagents is labelled with a binding reagent either for the analyte or for a binding reagent for the analyte.

4. The assay device according to claim 1, wherein the gas generating means generates oxygen gas.

5. The assay device of claim 1, further comprising a detection means to detect any alteration in flow of the liquid and/or an indicator region provided downstream of the accumulation zone to detect the presence or arrival of liquid.

6. The assay device of claim 1, wherein the indicator means comprises a non-electronic assay result indicator means.

7. The assay device of claim 1, wherein the device does not comprise, either any elements which require a power source, and/or a power source.

8. The assay device of claim 1, wherein the said one or more bubbles in the liquid sample halt or block the flow of liquid along the flow path.

9. The assay device of claim 1, wherein the bubble-retaining means is selected from the group consisting of: a neck or narrowed portion; overlapping projections in the flow path; and interdigitated projections on upper and lower surfaces of the flow path.

10. The assay device of claim 1, wherein the bubble-retaining means comprises a porous matrix.

11. The assay device of claim 10, wherein the porous matrix comprises a chromatographic membrane.

12. The assay device of claim 10, wherein the porous matrix is selected from nitrocellulose or filter paper.

* * * * *